United States Patent [19]

Imuta et al.

[11] Patent Number: 5,739,366

[45] Date of Patent: Apr. 14, 1998

[54] TRANSITION METAL COMPOUND CONTAINING SUBSTITUTED INDENYL RINGS

[75] Inventors: Junichi Imuta; Junji Saito; Takashi Ueda; Yoshihisa Kiso; Akira Mizuno; Masaaki Kawasaki, all of Yamaguchi, Japan

[73] Assignee: Mitsui Petrochemical Industries, Ltd., Tokyo, Japan

[21] Appl. No.: 479,606

[22] Filed: Jun. 7, 1995

Related U.S. Application Data

[62] Division of Ser. No. 255,713, Jun. 7, 1994, Pat. No. 5,504,172.

[30] Foreign Application Priority Data

| Jun. 7, 1993 | [JP] | Japan | 5-136255 |
| Jun. 28, 1993 | [JP] | Japan | 5-157367 |
| Sep. 24, 1993 | [JP] | Japan | 5-238562 |
| Oct. 6, 1993 | [JP] | Japan | 5-250743 |
| Nov. 22, 1993 | [JP] | Japan | 5-292071 |

[51] Int. Cl.$^6$ ................... C08F 4/64; C07F 7/00

[52] U.S. Cl. ................... 556/11; 556/12; 556/52; 556/53; 502/117; 502/152; 526/127; 526/160; 526/943

[58] Field of Search ................... 556/11, 12, 52, 556/53

[56] References Cited

U.S. PATENT DOCUMENTS

| 4,769,510 | 9/1988 | Kaminsky et al. |
| 5,243,001 | 9/1993 | Winter et al. |
| 5,278,264 | 1/1994 | Spaleck et al. |
| 5,304,614 | 4/1994 | Winter et al. |
| 5,328,969 | 7/1994 | Winter et al. |
| 5,332,789 | 7/1994 | Tanaka et al. |
| 5,336,746 | 8/1994 | Tsutsui et al. |

FOREIGN PATENT DOCUMENTS

| 0251771 | 1/1988 | European Pat. Off. |
| 0277003 | 8/1988 | European Pat. Off. |
| 0277004 | 8/1988 | European Pat. Off. |
| 0374695 | 6/1990 | European Pat. Off. |
| 426637 | 5/1991 | European Pat. Off. |
| 426638 | 5/1991 | European Pat. Off. |
| 427696 | 5/1991 | European Pat. Off. |
| 427697 | 5/1991 | European Pat. Off. |
| 468651 | 1/1992 | European Pat. Off. |
| 0537686 | 4/1993 | European Pat. Off. |
| 301704 | 1/1989 | Japan. |

OTHER PUBLICATIONS

Rubber Chemistry and Technology, pp. 781–804 (1971).

Macromolecules, vol. 8, No. 5, pp. 687–689, Sep.–Oct. (1975).

(List continued on next page.)

*Primary Examiner*—David W. Wu
*Attorney, Agent, or Firm*—Sherman and Shalloway

[57] ABSTRACT

The novel transition metal compound of the invention is represented by the following formula (I):

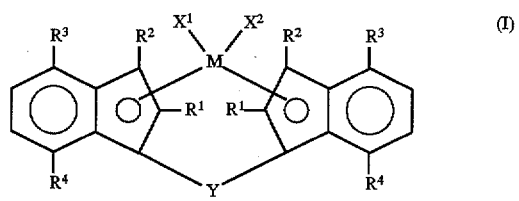

wherein M is a transition metal; $R^1$ and $R^2$ are each a hydrogen atom, a hydrocarbon group or the like; $R^3$ is an alkyl group of 2 to 20 carbon atoms; $R^4$ is an alkyl group of 2 to 20 carbon atoms; $X^1$ and $X^2$ are each a halogen atom or the like; and Y is a divalent hydrocarbon group, a divalent silicon-containing group or the like. The transition metal compound is useful for an olefin polymerization catalyst with which a propylene (co)polymer having specific structure is prepared.

4 Claims, 3 Drawing Sheets

OTHER PUBLICATIONS

Makromol. Chem., Rapid Commun. 8, pp. 305–310 (1987).
Journal of Molecular Catalysis, 56, pp. 237–247 (1989).
Polymer, vol. 30, pp. 1350–1356, Jul. (1989).
Polymer Preprints, Japan, vol. 39, No. 6, (1990) (No English Translation).

Angewandte Chemie, Internat'l Ed., vol. 31, No. 10, Oct. 1992, Weinheim De, XP00319626, W. Spaleck "High Molecular Weight . . . Zirconocene Catalysts" J Applied Polymer Science: Applied Polymer Symposium 52, pp. 159–172 (1993).

TRANSITION METAL COMPOUND CONTAINING SUBSTITUTED INDENYL RINGS

This is a division of application Ser. No. 08/255,713, filed Jun. 7, 1994, now U.S. Pat. No. 5,504,172.

FIELD OF THE INVENTION

The present invention relates to a novel transition metal compound, an olefin polymerization catalyst component comprising the transition metal compound, an olefin polymerization catalyst containing the catalyst component and a process for olefin polymerization using the olefin polymerization catalyst. The invention also relates to a propylene polymer, a propylene copolymer and a propylene elastomer, all having a high triad tacticity of the propylene unit chain.

BACKGROUND OF THE INVENTION

A well known homogeneous catalyst is, for example, so-called Kaminsky catalyst. Use of this Kaminsky catalyst produces a polymer having an extremely high polymerization activity and a narrow molecular weight distribution.

Of the Kaminsky catalysts, ethylenebis(indenyl)-zirconium dichloride and ethylenebis(4,5,6,7-tetrahydroindenyl)zirconium dichloride are known as transition metal compounds for preparing isotactic polyolefins, as described in Japanese Patent Laid-Open Publication No. 130314/1986. However, polyolefins prepared by the use of these catalysts generally have a low stereoregularity and a low molecular weight. As a process for preparing polyolefins of high stereoregularity and high molecular weight using these catalyst, there is a process in which the polymerization is conducted at a low temperature, but this process has a problem of low polymerization activity.

It is known that use of hafnium compounds in place of the zirconium compounds makes it possible to prepare a polymer having high molecular weight, as described in "Journal of Molecular Catalysis", 56(1989), pp. 237–247, but this process also has a problem of low polymerization activity. Further, dimethylsilyl bissubstituted cyclopentadienyl zirconium dichloride is also known as described in Japanese Patent Laid-Open Publication No. 301704/1989 and "Polymer Preprints", Japan, vol. 39, No. 6, pp. 1,614–1,616 (1990), but this compound is not satisfactory in all of polymerization activity, and stereoregularity and molecular weight of polymers obtained.

In order to solve these problems, various proposals have been made. For example, Japanese Patent Laid-Open Publication 268307/1993 describes an olefin polymerization catalyst formed from a metallocene compound represented by the following formula and aluminoxane as a catalyst capable of preparing a high molecular polyolefin, but the molecular weight of the resultant polyolefin is still insufficient.

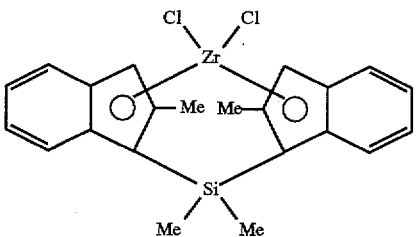

Further, EP 0 530 648A1 describes an olefin polymerization catalyst formed from a metallocene compound represented by the following formula and aluminoxane.

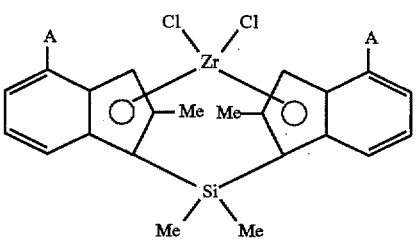

wherein A is a lower alkyl group.

The molecular weight of the polyolefin obtained by the use of this catalyst is high and industrially satisfactory. In addition, since the melting point of the polyolefin (e.g., polypropylene) having high stereoregularity becomes high, the catalyst is suitably used for preparing a stereoregular polyolefin having a high melting point. However, it is unsuitable for preparing a stereoregular polyolefin (particularly a copolymer) having a high molecular weight and a low melting point, and the resultant polyolefin or copolymer is not satisfactory in its quality.

Furthermore, EP 0 537 686 describes an olefin polymerization catalyst formed from a metallocene compound represented by the following formula and aluminoxane.

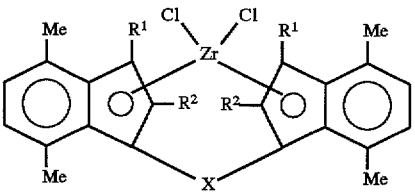

wherein $R^1$ and $R^2$ are each a methyl group or hydrogen, X is $Si(CH_3)_2$ group or an ethylene group.

However, a polyolefin obtained by the use of this catalyst is low in the molecular weight and cannot be practically used.

Under such circumstances as mentioned above, an olefin polymerization catalyst and a process for olefin polymerization, both having high olefin polymerization activity and being capable of preparing a polyolefin of excellent properties, are desired. Further, also desired are an olefin polymerization catalyst component used for such catalyst and a novel transition metal compound capable of forming the olefin polymerization catalyst component. In the light of the existing circumstances, the present inventors have earnestly studied, and as a result, they have found that the above requirements are satisfied by a transition metal compound which has two indenyl groups having a specific substituent group, said two indenyl groups being linked by way of a hydrocarbon group, a silicon-containing group or the like.

Propylene polymers have been applied to various uses because of their excellent mechanical properties and optical properties. For example, a propylene homopolymer is excellent in rigidity, surface hardness, heat resistance, glossiness and transparency, and hence it is used for various industrial parts, containers, films and nonwoven fabrics. A propylene/ethylene random copolymer containing a small amount of ethylene units is excellent in transparency, ridigity, surface hardness, heat resistance, heat-sealing properties, and hence it is used for films, containers, etc. A propylene elastomer is excellent in impact absorbing properties, heat resistance and heat-sealing properties, and hence it is singly used for films or used as a modifier of a thermoplastic resin.

However, the conventional propylene polymer is not always sufficient in transparency, impact resistance, etc. for some uses, and therefore the advent of a propylene polymer excellent in rigidity, heat resistance, surface hardness, glossiness, transparency and impact strength is desired. The conventional propylene/ethylene random copolymer is not always sufficient in transparency, heat-sealing properties, anti-blocking properties, bleed resistance, impact strength, etc. for some uses, and therefore the advent of a propylene/ethylene random copolymer excellent in transparency, rigidity, surface harness, heat resistance and heat-sealing properties is desired. The conventional propylene elastomer is not always sufficient in heat-sealing properties, anti-blocking properties and heat resistance when used singly, and is not always sufficient in effect of improving impact resistance when used as a modifier. Therefore, a propylene elastomer excellent in impact resistance, heat resistance, transparency, heat-sealing properties, anti-blocking properties and effect of improving impact resistance is desired.

In the light of such circumstances as described above, the present inventors have further studied, and as a result, they have found that a propylene homopolymer having a high triad tacticity, as measured by $^{13}$C-NMR, of the propylene chain consisting of head-to-tail bonds, a specific proportion of inversely inserted propylene units and a specific intrinsic viscosity is excellent in the above-mentioned properties. Further, they have also found that a propylene copolymer which contains a small amount of ethylene units and has a high triad tacticity, as measured by $^{13}$C-NMR, of the propylene chain consisting of head-to-tail bonds, a specific proportion of inversely inserted propylene units and a specific intrinsic viscosity is excellent in the above-mentioned properties. Furthermore, they have found that a propylene elastomer which contains a specific amount of ethylene units and has a high triad tacticity, as measured by $^{13}$C-NMR, of the propylene chain consisting of head-to-tail bonds, a specific proportion of inversely inserted propylene units and a specific intrinsic viscosity is excellent in the above-mentioned properties.

Moreover, the present inventors have found that the propylene polymer, the propylene copolymer and the propylene elastomer can be prepared by the use of an olefin polymerization catalyst containing the aforesaid specific transition metal compound as a catalyst component.

OBJECT OF THE INVENTION

It is an object of the present invention to provide a novel transition metal compound useful for an olefin polymerization catalyst component having a high olefin polymerization activity and to provide an olefin polymerization catalyst component comprising said transition metal compound.

It is another object of the invention to provide an olefin polymerization catalyst containing the above olefin polymerization catalyst component and to provide a process for olefin polymerization using said olefin polymerization catalyst.

It is a further object of the invention to provide a propylene polymer having excellent properties.

SUMMARY OF THE INVENTION

The novel transition metal compound according to the invention is a transition metal compound represented by the following formula (I):

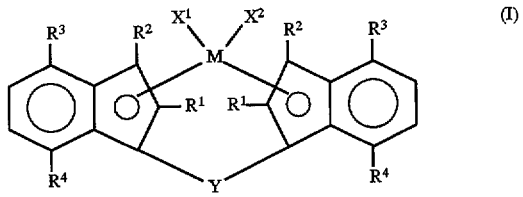

wherein M is a transition metal of Group IVa, Group Va and Group VIa of the periodic table;

$R^1$ and $R^2$ are each a hydrogen atom, a halogen atom, a hydrocarbon group of 1 to 20 carbon atoms, a halogenated hydrocarbon group of 1 to 20 carbon atoms, a silicon-containing group, an oxygen-containing group, a sulfur-containing group, a nitrogen-containing group or a phosphorus-containing group;

$R^3$ is an alkyl group of 2 to 20 carbon atoms;

$R^4$ is an alkyl group of 1 to 20 carbon atoms;

$X^1$ and $X^2$ are each a hydrogen atom, a halogen atom, a hydrocarbon group of 1 to 20 carbon atoms, a halogenated hydrocarbon group of 1 to 20 carbon atoms, an oxygen-containing group or a sulfur-containing group; and Y is a divalent hydrocarbon group of 1 to 20 carbon atoms, a divalent halogenated hydrocarbon group of 1 to 20 carbon atoms, a divalent silicon-containing group, a divalent germanium-containing group, a divalent tin-containing group, —O—, —CO—, —S—, —SO—, —SO$_2$—, —NR$^5$—, —P(R$^5$)—, —P(O)(R$^5$)—, —BR$^5$— or —AlR$^5$— (R$^5$ is a hydrogen atom, a halogen atom, a hydrocarbon group of 1 to 20 carbon atoms or a halogenated hydrocarbon group of 1 to 20 carbon atoms).

The olefin polymerization catalyst component according to the invention comprises a transition metal compound represented by the above formula (I).

The first olefin polymerization catalyst according to the invention comprises:

(A) a transition metal compound represented by the above formula (I); and (B) at least one compound selected from a group consisting of (B-1) an organoaluminum oxy-compound, and (B-2) an compound which reacts with the transition metal compound to form an ion pair.

The second olefin polymerization catalyst according to the invention comprises:

(A) a transition metal compound represented by the above formula (I);

(B) at least one compound selected from a group consisting of (B-1) an organoaluminum oxy-compound, and (B-2) an compound which reacts with the transition metal compound to form an ion pair; and (C) an organoaluminum compound.

The third olefin polymerization catalyst according to the invention comprises:

a fine particle carrier;
  (A) a transition metal compound represented by the above formula (I); and
  (B) at least one compound selected from a group consisting of
    (B-1) an organoaluminum oxy-compound, and
    (B-2) an compound which reacts with the transition metal compound to form an ion pair;
  said transition metal compound (A) and said at least one compound (B) being supported on the fine particle carrier.

The fourth olefin polymerization catalyst according to the invention comprises:
a solid catalyst component comprising:
  a fine particle carrier,
  (A) a transition metal compound represented by the above formula (I), and
  (B) at least one compound selected from a group consisting of
    (B-1) an organoaluminum oxy-compound, and
    (B-2) an compound which reacts with the transition metal compound to form an ion pair,
  said transition metal compound (A) and said at least one compound (B) being supported on the fine particle carrier; and
  (C) an organoaluminum compound.

The fifth olefin polymerization catalyst according to the invention comprises:
a fine particle carrier;
  (A) a transition metal compound represented by the above formula (I);
  (B) at least one compound selected from a group consisting of
    (B-1) an organoaluminum oxy-compound, and
    (B-2) an compound which reacts with the transition metal compound to form an ion pair; and
a prepolymerized olefin polymer produced by prepolymerization.

The sixth olefin polymerization catalyst according to the invention comprises:
a fine particle carrier;
  (A) a transition metal compound represented by the above formula (I);
  (B) at least one compound selected from a group consisting of
    (B-1) an organoaluminum oxy-compound, and
    (B-2) an compound which reacts with the transition metal compound to form an ion pair;
  (C) an organoaluminum compound; and
a prepolymerized olefin polymer produced by prepolymerization.

The process for olefin polymerization according to the invention comprises polymerizing or copolymerizing an olefin in the presence of any of the first to sixth olefin polymerization catalysts.

The olefin polymerization catalysts according to the invention have high polymerization activity and an olefin polymer obtained by using the catalytsts has a narrow molecular weight distribution and a narrow composition distribution. When they are used for polymerizing an α-olefin of 3 or more carbon atoms, obtainable is a polymer having a lower melting point as compared with a polymer obtained by using a conventional metallocene catalyst when these polymers have similar molecular weights. Further, in the preparation of a copolymer elastomer containing ethylene or propylene as its major component, a polymer of high molecular weight can be obtained.

When such catalysts are used, a copolymer having a low melting point can be obtained even though an amount of comonomer units is small.

The propylene polymer according to the invention has such properties that:
(a) a triad tacticity of three propylene units-chain consisting of head-to-tail bonds, as measured by $^{13}$C-NMR, is not less than 90.0%;
(b) a proportion of the inversely inserted propylene units based on the 2,1-insertion of a propylene monomer in all propylene insertions, as measured by $^{13}$C-NMR, is not less than 0.7%, and the proportion of the inversely inserted propylene units based on the 1,3-insertion of a propylene monomer, as measured by $^{13}$C-NMR, is not more than 0.05%; and
(c) the intrinsic viscosity, as measured in decahydronaphthalene at 135° C., is in the range of 0.1 to 12 dl/g.

Such propylene polymer is excellent in rigidity, heat resistance, surface hardness, glossiness, transparency and impact resistance.

The propylene copolymer according to the invention has such properties that:
(a) said copolymer contains propylene units in an amount of 95 to 99.5% by mol and ethylene units in an amount of 0.5 to 5% by mol;
(b) a triad tacticity of three propylene units-chain consisting of head-to-tail bonds, as measured by $^{13}$C-NMR, is not less than 90.0%;
(c) a proportion of inversely inserted propylene units based on the 2,1-insertion of a propylene monomer in all propylene insertions, as measured by $^{13}$C-NMR, is not less than 0.5%, and a proportion of inversely inserted propylene units based on the 1,3-insertion of a propylene monomer, as measured by $^{13}$C-NMR, is not more than 0.05%; and
(d) the intrinsic viscosity, as measured in decahydronaphthalene at 135° C., is in the range of 0.1 to 12 dl/g.

Such propylene copolymer is excellent in transparency, rigidity, surface hardness, heat resistance, heat-sealing properties, bleed resistance and impact resistance.

The propylene elastomer according to the invention has such properties that:
(a) said elastomer contains propylene units in an amount of 50 to 95% by mol and ethylene units in an amount of 5 to 50% by mol;
(b) a triad tacticity of three propylene units-chain consisting of head-to-tail bonds, as measured by $^{13}$C-NMR, is not less than 90.0%;
(c) a proportion of inversely inserted propylene units based on the 2,1-insertion of a propylene monomer in all propylene insertions, as measured by $^{13}$C-NMR, is not less than 0.5%, and a proportion of inversely inserted propylene units based on the 1,3-insertion of a propylene monomer, as measured by $^{13}$C-NMR, is not more than 0.05%; and
(d) the intrinsic viscosity, as measured in decahydronaphthalene at 135° C., is in the range of 0.1 to 12 dl/g.

Such propylene elastomer is excellent in heat resistance, impact absorbing properties, transparency, heat-sealing properties and anti-blocking properties.

DETAILED DESCRIPTION OF THE INVENTION

The novel transition metal compound, the olefin polymerization catalyst component comprising the transition metal compound, the olefin polymerization catalyst containing the olefin polymerization catalyst component, the process for olefin polymerization using the olefin polymerization catalyst, the propylene polymer, the propylene copolymer and the propylene elastomer, according to the invention, will be described in detail hereinafter.

Figure 1:
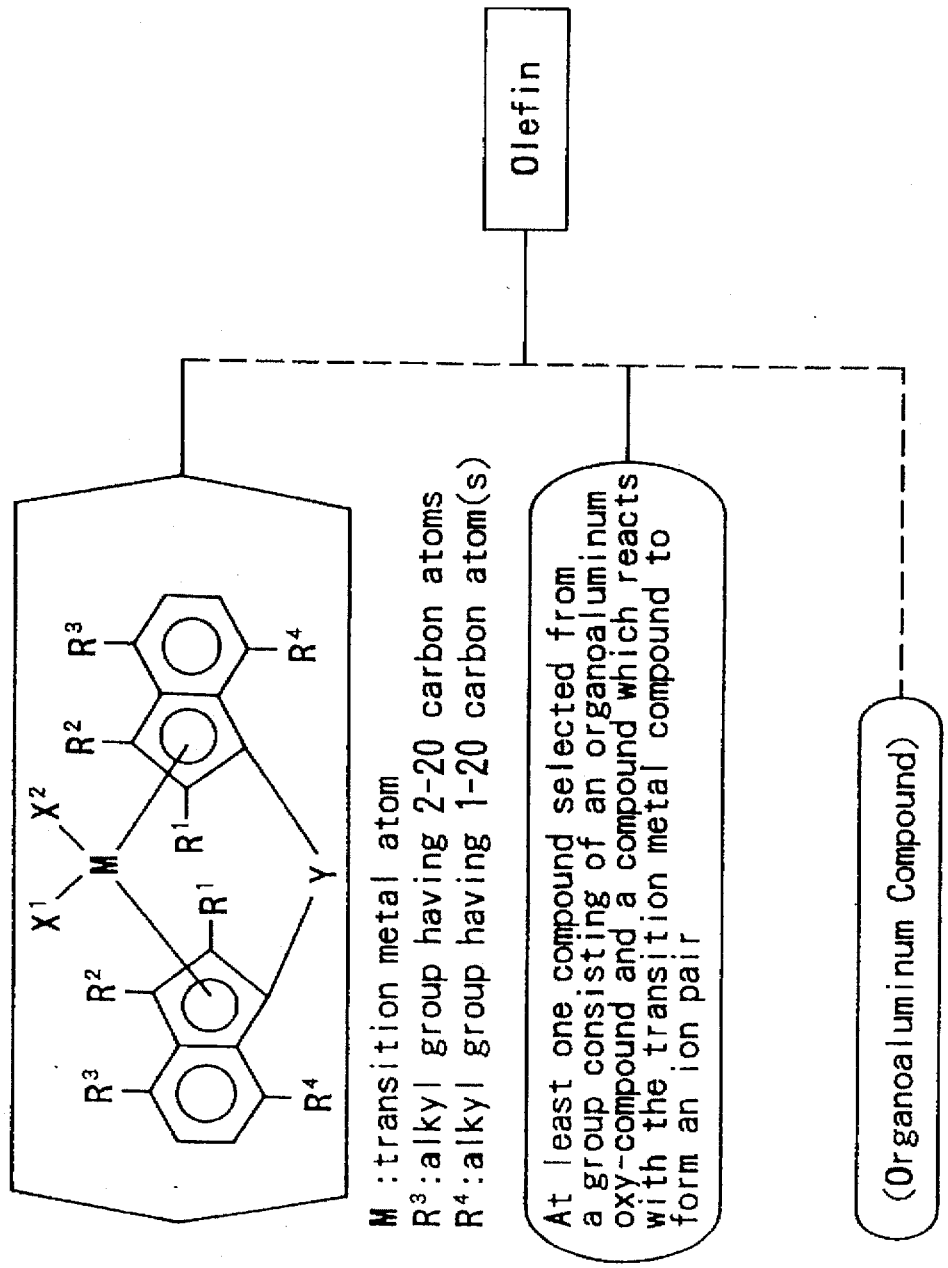
FIG. 1 is a view illustrating steps of a process for preparing the first and the second olefin polymerization catalysts according to the invention.
Figure 2:
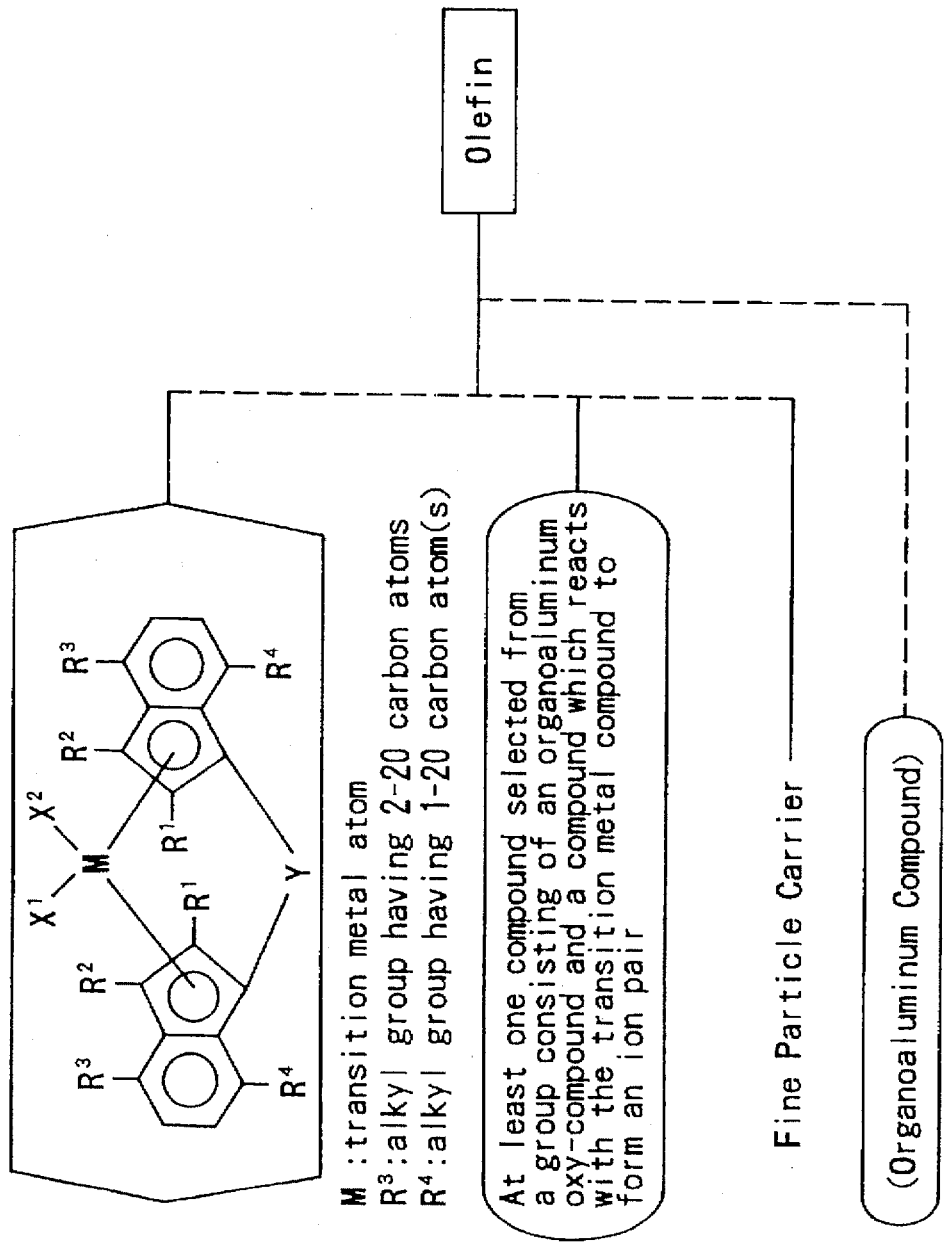
FIG. 2 is a view illustrating steps of a process for preparing the third and the fourth olefin polymerization catalysts according to the invention.
Figure 3:
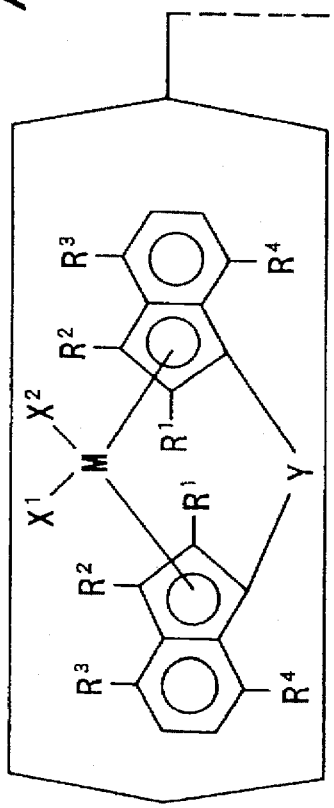
FIG. 3 is a view illustrating steps of a process for preparing the fifth and the sixth olefin polymerization catalysts according to the invention.

FIG. 1 is a view illustrating steps of a process for preparing the first and the second olefin polymerization catalysts according to the invention. FIG. 2 is a view illustrating steps of a process for preparing the third and the fourth olefin polymerization catalysts according to the invention. FIG. 3 is a view illustrating steps of a process for preparing the fifth and the sixth olefin polymerization catalysts according to the invention.

First, the novel transition metal compound according to the invention is described.

The novel transition metal compound of the invention is a transition metal compound represented by the following formula (I).

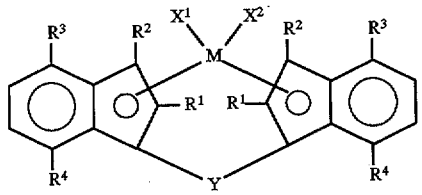

In the formula (I), M is a transition metal of Group IVa, Group Va and Group VIa of the periodic table. Examples of the transition metals include titanium, zirconium, hafnium, vanadium, niobium, tantalum, chromium, molybdenum and tungsten. Of these, titanium, zirconium and hafnium are preferred, and zirconium is particularly preferred.

$R^1$ and $R^2$ are each independently a hydrogen atom, a halogen atom, a hydrocarbon group of 1 to 20 carbon atoms, a halogenated hydrocarbon group of 1 to 20 carbon atoms, a silicon-containing group, an oxygen-containing group, a sulfur-containing group, a nitrogen-containing group or a phosphorus-containing group.

Examples of the halogen atoms include fluorine, chlorine, bromine and iodine.

Examples of the hydrocarbon groups of 1 to 20 carbon atoms include an alkyl group such as methyl, ethyl, propyl, butyl, hexyl, cyclohexyl, octyl, nonyl, dodecyl, icosyl, norbornyl and adamantyl; an alkenyl group such as vinyl, propenyl and cyclohexenyl; arylalkyl group such as benzyl, phenylethyl and phenylpropyl; and an aryl group such as phenyl, tolyl, dimethylphenyl, trimethylphenyl, ethylphenyl, propylphenyl, biphenyl, naphthyl, methylnaphthyl, anthracenyl and phenanthryl.

Examples of the halogenated hydrocarbon groups include halogenated hydrocarbon groups of the above-mentioned hydrocarbon groups.

Examples of the silicon-containing groups include monohydrocarbon-substituted silyl such as methylsilyl and phenylsilyl; dihydrocarbon-substituted silyl such as dimethylsilyl and diphenylsilyl; trihydrocarbon-substituted silyl such as trimethylsilyl, triethylsilyl, tripropylsilyl, tricyclohexylsilyl, triphenylsilyl, dimethylphenylsilyl, methyldiphenylsilyl, tritolylsilyl and trinaphthylsilyl; silyl ether, of hydrocarbon-substituted silyl such as trimethylsilyl ether; silicon-substituted alkyl group such as trimethylsilylmethyl; and silicon-substituted aryl group such as trimethylphenyl.

Examples of the oxygen-containing groups include a hydroxy group; an alkoxy group such as methoxy, ethoxy, propoxy and butoxy; an allyloxy group such as phenoxy, methylphenoxy, dimethylphenoxy and naphthoxy; and an arylalkoxy group such as phenylmethoxy and phenylethoxy.

Examples of the sulfur-containing groups include groups obtained by substituting sulfur for oxygen in the above-mentioned oxygen-containing groups.

Examples of the nitrogen-containing groups include an amino group; an alkylamino group such as methylamino, dimethylamino, diethylamino, dipropylamino, dibutylamino and dicyclohexylamino; an arylamino group such as phenylamino, diphenylamino, ditolylamino, dinaphthylamino and methylphenylamino; and an alkylarylamino group.

Examples of the phosphorus-containing groups include a phosphino group such as dimethylphosphino and diphenylphosphino.

Of these, $R^1$ is preferably a hydrocarbon group, particularly a hydrocarbon group of 1 to 3 carbon atoms such as methyl, ethyl and propyl. $R^2$ is preferably a hydrogen atom or a hydrocarbon group, particularly a hydrogen atom or a hydrocarbon group of 1 to 3 carbon atoms such as methyl, ethyl and propyl.

$R^3$ is an alkyl group of 2 to 20 carbon atom, and $R^4$ is an alkyl group of 1 to 20 carbon atoms. $R^3$ is preferably a secondary or tertiary alkyl group. The alkyl group indicated by $R^3$ or $R^4$ may be substituted with a halogen atom or a silicon-containing group. Examples of the halogen atoms and examples or the silicon-containing groups are those exemplified above with respect to $R^1$ and $R^2$.

Examples of the alkyl groups indicated by $R^3$ include: a chain alkyl group and a cyclic alkyl group, such as ethyl, n-propyl, i-propyl, n-butyl, i-butyl, sec-butyl, tert-butyl, pentyl, hexyl, cyclohexyl, heptyl, octyl, nonyl, dodecyl, icosyl, norbornyl and adamantyl; and an arylalkyl group, such as benzyl, phenylethyl, phenylpropyl and tolylmethyl.

These groups may be substituted with groups containing a double bond or a triple bond.

Examples of the alkyl groups indicated by $R^4$ include methyl, and the chain alkyl groups, the cyclic alkyl groups and the arylalkyl groups exemplified above with respect to $R^3$.

$X^1$ and $X^2$ are each a hydrogen atom, a halogen atom, a hydrocarbon group of 1 to 20 carbon atoms, a halogenated hydrocarbon group of 1 to 20 carbon atoms, an oxygen-containing group or a sulfur-containing group. Examples of those atoms and groups include the halogen atoms, the hydrocarbon groups of 1 to 20 carbon atoms, the halogenated hydrocarbon groups of 1 to 20 carbon atoms and the oxygen-containing groups exemplified above with respect to $R^1$ and $R^2$.

As the sulfur-containing group, there can be mentioned a sulfonato group such as methylsulfonato, trifluoromethanesulfonato, phenylsulfonato, benzylsulfonato, p-toluenesulfonato, trimethyibenzenesulfonato, triisobutylbenzenesulfonato, p-chlorobenzenesulfonato and pentafluorobenzenesulfonato; and a sulfinato group such as methylsulfinato, phenylsulfinato, benzenesulfinato, p-toluenesulfinato, trimethyibenzenesulfinato and pentafluorobenzenesulfinato.

Y is a divalent hydrocarbon group of 1 to 20 carbon atoms, a divalent halogenated hydrocarbon group of 1 to 20 carbon atoms, a divalent silicon-containing group, a divalent germanium-containing group, a divalent tin-containing group, —O—, —CO—, —S—, —SO—, —SO$_2$—, —NR$^5$—, —P(R$^5$)—, —P(O)(R$^5$)—, —BR$^5$— or —AlR$^5$— (R$^5$ is a hydrogen atom, a halogen atom, a hydrocarbon group of 1 to 20 carbon atoms or a halogenated hydrocarbon group of 1 to 20 carbon atoms).

Examples of the divalent hydrocarbon groups of 1 to 20 carbon atoms include an alkylene group such as methylene, dimethylmethylene, 1,2-ethylene, dimethyl-1,2-ethylene, 1,3-trimethylene, 1,4-tetramethylene, 1,2-cyclohexylene and 1,4-cyclohexylene; and an arylalkylene group such as diphenylmethylene and diphenyl-1,2-ethylene.

Examples of the halogenated hydrocarbon groups include groups obtained by halogenating the above-mentioned hydrocarbon groups of 1 to 20 carbon atoms, such as chloromethylene.

Examples of the silicon-containing groups include an alkylsilylene group, an alkylarylsilylene group and an arylsilylene group, such as methylsilylene, dimethylsilylene, diethylsilylene, di(n-propyl)silylene, di(i-propyl)silylene, di(cyclohexyl)silylene, methylphenylsilylene, diphenylsilylene, di(p-tolyl)silylene and di(p-chlorophenyl)silylene; and an alkyldisilyl group, an alkylaryldisilyl group and an arylsilyl group, such as tetramethyl-1,2-disilyl and tetraphenyl-1,2-disilyl.

Examples of the divalent germanium-containing groups include groups obtained by substituting germanium for silicon in the above-mentioned divalent silicon-containing groups.

Examples of the divalent tin-containing groups include groups obtained by substituting tin for silicon in the above-mentioned divalent silicon-containing groups.

Examples of the atoms and the groups indicated by R$^5$ include the hydrogen atoms, the halogen atoms, the hydrocarbon groups of 1 to 20 carbon atoms and the halogenated hydrocarbon groups of 1 to 20 carbon atoms exemplified above with respect to R$^1$ and R$^2$.

Of these, preferred are a divalent silicon-containing group, a divalent germanium-containing group and a divalent tin-containing group. More preferred is a silicon-containing group. Of the silicon-containing groups, alkylsilylene, alkylarylsilylene and arylsilylene are particularly preferred.

Listed below are examples of the transition metal compounds represented by the above formula (I).

rac-Dimethylsilyl-bis{1-(2,7-dimethyl-4-ethylindenyl)}zirconium dichloride, rac-Dimethylsilyl-bis{1-(2,7-dimethyl-4-n-propylindenyl)}zirconium dichloride, rac-Dimethylsilyl-bis{1-(2,7-dimethyl-4-i-propylindenyl)}zirconium dichloride, rac-Dimethylsilyl-bis{1-(2,7-dimethyl-4-n-butylindenyl)}zirconium dichloride, rac-Dimethylsilyl-bis{1-(2,7-dimethyl-4-sec-butylindenyl)}zirconium dichloride, rac-Dimethylsilyl-bis{1-(2,7-dimethyl-4-t-butylindenyl)}zirconium dichloride, rac-Dimethylsilyl-bis{1-(2,7-dimethyl-4-n-pentylindenyl)}zirconium dichloride, rac-Dimethylsilyl-bis{1-(2,7-dimethyl-4-n-hexylindenyl)}zirconium dichloride, rac-Dimethylsilyl-bis{1-(2,7-dimethyl-4-cyclohexylindenyl)}zirconium dichloride, rac-Dimethylsilyl-bis{1-(2,7-dimethyl-4-methylcyclohexylindenyl)}zirconium dichloride, rac-Dimethylsilyl-bis{1-(2,7-dimethyl-4-phenylethylindenyl)}zirconium dichloride, rac-Dimethylsilyl-bis{1-(2,7-dimethyl-4-phenyldichloromethylindenyl)}zirconium dichloride, rac-Dimethylsilyl-bis{1-(2,7-dimethyl-4-chloromethylindenyl)}zirconium dichloride, rac-Dimethylsilyl-bis{1-(2,7-dimethyl-4-trimethylsilylmethylindenyl)}zirconium dichloride, rac-Dimethylsilyl-bis{1-(2,7-dimethyl-4-trimethylsiloxymethylindenyl)}zirconium dichloride, rac-Diethylsilyl-bis{1-(2,7-dimethyl-4-i-propylindenyl)}zirconium dichloride, rac-Di(i-propyl)silyl-bis{1-(2,7-dimethyl-4-i-propylindenyl)}zirconium dichloride, rac-Di(n-butyl)silyl-bis{1-(2,7-dimethyl-4-i-propylindenyl)}zirconium dichloride, rac-Di(cyclohexyl)silyl-bis{1-(2,7-dimethyl-4-i-propylindenyl)}zirconium dichloride, rac-Methylphenylsilyl-bis{1-(2,7-dimethyl-4-i-propylindenyl)}zirconium dichloride, rac-Methylphenylsilyl-bis{1-(2,7-dimethyl-4-t-butylindenyl)}zirconium dichloride, rac-Diphenylsilyl-bis{1-(2,7-dimethyl-4-t-butylindenyl)}zirconium dichloride, rac-Diphenylsilyl-bis{1-(2,7-dimethyl-4-i-propylindenyl)}zirconium dichloride, rac-Diphenylsilyl-bis{1-(2,7-dimethyl-4-ethylindenyl)}zirconium dichloride, rac-Di(p-tolyl)silyl-bis{1-(2,7-dimethyl-4-i-propylindenyl)}zirconium dichloride, rac-Di(p-chlorophenyl)silyl-bis{1-(2,7-dimethyl-4-i-propylindenyl)}zirconium dichloride, rac-Dimethylsilyl-bis{1-(2-methyl-4-i-propyl-7-ethylindenyl)}zirconium dibromide, rac-Dimethylsilyl-bis{1-(2,3,7-trimethyl-4-ethylindenyl)}zirconium dichloride, rac-Dimethylsilyl-bis{1-(2,3,7-trimethyl-4-n-propylindenyl)}zirconium dichloride, rac-Dimethylsilyl-bis{1-(2,3,7-trimethyl-4-i-propylindenyl)}zirconium dichloride, rac-Dimethylsilyl-bis{1-(2,3,7-trimethyl-4-n-butylindenyl)}zirconium dichloride, rac-Dimethylsilyl-bis{1-(2,3,7-trimethyl-4-sec-butylindenyl)}zirconium dichloride, rac-Dimethylsilyl-bis{1-(2,3,7-trimethyl-4-t-butylindenyl)}zirconium dichloride, rac-Dimethylsilyl-bis{1-(2,3,7-trimethyl-4-n-pentylindenyl)}zirconium dichloride, rac-Dimethylsilyl-bis{1-(2,3,7-trimethyl-4-n-hexylindenyl)}zirconium dichloride, rac-Dimethylsilyl-bis{1-(2,3,7-trimethyl-4-cyclohexylindenyl)}zirconium dichloride, rac-Dimethylsilyl-bis{1-(2,3,7-trimethyl-4-methylcyclohexylindenyl)}zirconium dichloride,
rac-Dimethylsilyl-bis{1-(2,3,7-trimethyl-4-trimethylsilylmethylindenyl)}zirconium dichloride,
rac-Dimethylsilyl-bis{1-(2,3,7-trimethyl-4-trimethylsiloxymethylindenyl)}zirconium dichloride,
rac-Dimethylsilyl-bis{1-(2,3,7-trimethyl-4-phenylethylindenyl)}zirconium dichloride,
rac-Dimethylsilyl-bis{1-(2,3,7-trimethyl-4-phenyldichloromethylindenyl)}zirconium dichloride,
rac-Dimethylsilyl-bis{1-(2,3,7-trimethyl-4-chloromethylindenyl)}zirconium dichloride,
rac-Diethylsilyl-bis{1-(2,3,7-trimethyl-4-i-propylindenyl)}zirconium dichloride,
rac-Di(i-propyl)silyl-bis{1-(2,3,7-trimethyl-4-i-propylindenyl)}zirconium dichloride,
rac-Di(n-butyl)silyl-bis{1-(2,3,7-trimethyl-4-i-propylindenyl)}zirconium dichloride,
rac-Di(cyclohexyl)silyl-bis{1-(2,3,7-trimethyl-4-i-propylindenyl)}zirconium dichloride,
rac-Methylphenylsilyl-bis{1-(2,3,7-trimethyl-4-i-propylindenyl)}zirconium dichloride,
rac-Methylphenylsilyl-bis{1-(2,3,7-trimethyl-4-t-butylindenyl)}zirconium dichloride,
rac-Diphenylsilyl-bis{1-(2,3,7-trimethyl-4-t-butylindenyl)}zirconium dichloride,
rac-Diphenylsilyl-bis{1-(2,3,7-trimethyl-4-i-propylindenyl)}zirconium dichloride,
rac-Diphenylsilyl-bis{1-(2,3,7-trimethyl-4-ethylindenyl)}zirconium dichloride,
rac-Di(p-tolyl)silyl-bis{1-(2,3,7-trimethyl-4-i-propylindenyl)}zirconium dichloride,
rac-Di(p-chlorophenyl)silyl-bis{1-(2,3,7-trimethyl-4-i-propylindenyl)}zirconium dichloride,
rac-Dimethylsilyl-bis{1-(2-methyl-4-i-propyl-7-methylindenyl)}zirconium dimethyl,
rac-Dimethylsilyl-bis{1-(2-methyl-4-i-propyl-7-methylindenyl)}zirconium methylchloride,
rac-Dimethylsilyl-bis{1-(2-methyl-4-i-propyl-7-methylindenyl)}zirconium-bis(methanesulfonate),
rac-Dimethylsilyl-bis{1-(2-methyl-4-i-propyl-7-methylindenyl)}zirconium-bis(p-phenylsulfonate),
rac-Dimethylsilyl-bis{1-(2-methyl-3-methyl-4-i-propyl-7-methylindenyl)}zirconium dichloride,
rac-Dimethylsilyl-bis{1-(2-ethyl-4-i-propyl-7-methylindenyl)}zirconium dichloride,
rac-Dimethylsilyl-bis{1-(2-phenyl-4-i-propyl-7-methylindenyl)}zirconium dichloride,
rac-Dimethylsilyl-bis{1-(2-methyl-4-i-propyl-7-methylindenyl)}titanium dichloride, and
rac-Dimethylsilyl-bis{1-(2-methyl-4-i-propyl-7-methylindenyl)}hafnium dichloride.

Of these, compounds having a branched alkyl group (e.g., i-propyl, sec-butyl and tert-butyl) at the fourth position are particularly preferred. In the present invention, also employable are transition metal compounds wherein the zirconium metal is substituted for titanium, hafnium, vanadium, niobium, tantalum, chromium, molybdenum or tungsten in the above-listed compounds.

The indene derivative ligand of the novel transition metal compound according to the invention can be synthesized by an organic synthesis method conventionally used through the following reaction route.

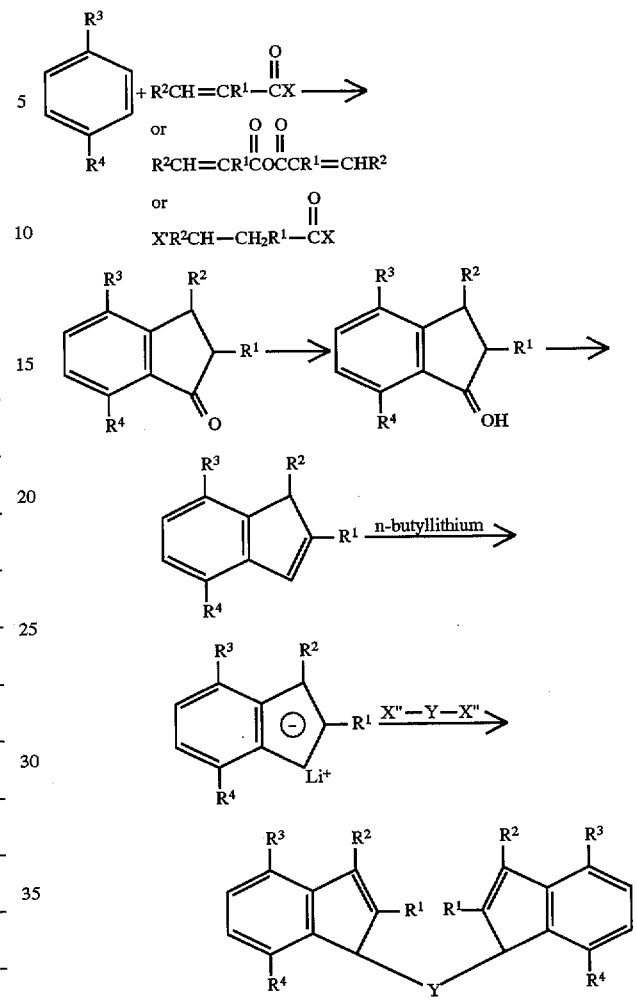

(wherein each of X, X' and X" is a halogen atom.)

The transition metal compound of the invention can be synthesized from the indene derivative by conventionally known methods, for example, a method described in Japanese Patent Laid-Open Publication No. 268307/1993.

The novel transition metal compound according to the invention can be used as an olefin polymerization catalyst component in combination with an organoaluminum oxycompound, etc.

The transition metal compound is used as an olefin polymerization catalyst component in the form of usually a racemic modification, but the R configuration or the S configuration can be also used.

Next, the olefin polymerization catalyst containing the above-mentioned novel transition metal compound as its catalyst component is described.

The meaning of the term "polymerization" used herein is not limited to "homopolymerization" but may comprehend "copolymerization". Also, the meaning of the term "polymer" used herein is not limited to "homopolymer" but may comprehend "copolymer".

The first and the second olefin polymerization catalysts according to the invention are described below.

The first olefin polymerization catalyst of the invention is formed from:

(A) a transition metal compound represented by the above formula (I) (sometimes referred to as "component (A)" hereinafter); and (B) at least one compound selected from a group consisting of
   (B-1) an organoaluminum oxy-compound, and
   (B-2) a compound which reacts with the transition metal compound to form an ion pair.

The second olefin polymerization catalyst of the invention is formed from:
(A) a transition metal compound represented by the above formula (I);
(B) at least one compound selected from a group consisting of
   (B-1) an organoaluminum oxy-compound, and
   (B-2) a compound which reacts with the transition metal compound to form an ion pair; and
(C) an organoaluminum compound.

The organoaluminum oxy-compound (B-1) (hereinafter sometimes referred to as "component (B-1)") used for the first and the second olefin polymerization catalysts of the invention may be a conventionally known aluminoxane or may be a benzene-insoluble organoaluminum oxy-compound as described in Japanese Patent Laid-Open Publication No. 78687/1990.

The conventionally known aluminoxane can be prepared, for example, by the following processes.

(1) A process comprising allowing an organoaluminum compound such as trialkylaluminum to react with a suspension of a compound having adsorbed water or a salt containing water of crystallization, for example, hydrate of magnesium chloride, copper sulfate, aluminum sulfate, nickel sulfate or cerous chloride in a hydrocarbon solvent.

(2) A process comprising allowing water, ice or water vapor to directly react with an organoaluminum compound such as trialkylaluminum in a solvent such as benzene, toluene, ethyl ether and tetrahydrofuran.

(3) A process comprising allowing an organotin oxide such as dimethyltin oxide and dibutyltin oxide to react with an organoaluminum compound such as trialkylaluminum in a solvent such as decane, benzene and toluene.

The aluminoxane may contain a small amount of an organometallic component. Moreover, the solvent or the unreacted organoaluminum compound may be distilled off from the recovered solution of aluminoxane described above, and the resultant product may be dissolved again in a solvent.

Examples of the organoaluminum compounds used for preparing aluminoxane include:

trialkylaluminums, such as trimethylaluminum, triethylaluminum, tripropylaluminum, triisopropylaluminum, tri-n-butylaluminum, triisobutylaluminum, tri-sec-butylaluminum, tri-tert-butylaluminum, tripentylaluminum, trihexylaluminum, trioctylaluminum and tridecylaluminum;

tricycloalkylaluminums, such as tricyclohexylaluminum and tricyclooctylaluminum;

dialkylaluminum halides, such as dimethylaluminum chloride, diethylaluminum chloride, diethylaluminum bromide and diisobutylaluminum chloride;

dialkylaluminum hydrides, such as diethylaluminum hydride and diisobutylaluminum hydride;

dialkylaluminum alkoxides, such as dimethylaluminum methoxide and diethylaluminum ethoxide; and dialkylaluminum aryloxides, such as diethylaluminum phenoxide.

Of the organoaluminum compounds, trialkylaluminum and tricycloalkylaluminum are particularly preferred.

Further, there may be also used, as the organoaluminum compound for preparing aluminoxane, isoprenylaluminum represented by the following formula (II):

$$(i\text{-}C_4H_9)_xAl_y(C_5H_{10})_z \qquad (II)$$

wherein x, y and z are each a positive number, and $z \leq 2x$.

The organoaluminum compounds mentioned above may be used singly or in combination.

Solvents used for preparing aluminoxane include aromatic hydrocarbons such as benzene, toluene, xylene, cumene and cymene; aliphatic hydrocarbons such as pentane, hexane, heptane, octane, decane, dodecane, hexadecane and octadecane; alicyclic hydrocarbons such as cyclopentane, cyclohexane, cyclooctane and methylcyclopentane; petroleum fractions such as gasoline, kerosine and gas oil; and halides of the above-mentioned aromatic, aliphatic and alicyclic hydrocarbons, particularly chlorides and bromides thereof. In addition thereto, ethers such as ethyl ether and tetrahydrofuran may be also used. Of these solvents, particularly preferred are aromatic hydrocarbons.

Examples of the compounds which react with the transition metal compound (A) to form an ion pair (hereinafter sometimes referred to as "component (B-2)"), which are used for the first and the second olefin polymerization catalysts, include Lewis acid, ionic compounds, borane compounds and carborane compounds, as described in National Publications of International Patent No. 501950/1989 and No. 502036/1989, Japanese Patent Laid-Open Publications No. 179005/1992, No. 179006/1992, No. 207703/1992 and No. 207704/1992, and U.S. Pat. No. 547,718.

The Lewis acid includes Mg-containing Lewis acid, Al-containing Lewis acid and B-containing Lewis acid. Of these, B-containing Lewis acid is preferred.

The Lewis acid containing a boron atom (B-containing Lewis acid) is, for example, a compound represented by the following formula:

$$BR^6R^7R^8$$

wherein $R^6$, $R^7$ and $R^8$ are each independently a phenyl group which may have a substituent such as a fluorine atom, a methyl group and a trifluoromethyl group, or a fluorine atom.

Examples of the compounds represented by the above formula include trifluoroboron, triphenylboron, tris(4-fluorophenyl)boron, tris(3,5-difluorophenyl)boron, tris(4-fluoromethylphenyl)boron, tris(pentafluorophenyl)boron, tris(p-tolyl)boron, tris(o-tolyl)boron and tris(3,5-dimethylphenyl)boron. Of these, tris(pentafluorophenyl) boron is particularly preferred.

The ionic compound used in the invention is a salt comprising a cationic compound and an anionic compound. An anion reacts with the transition metal compound (A) to make the transition metal compound (A) cationic and to form an ion pair so as to stabilize the transition metal cation seed. Examples of such anions include organoboron compound anion and organoarsenic compound anion, organoaluminum compound anion. Preferred is such anion as is relatively bulky and stabilizes the transition metal cation species. Examples of cations include metallic cation, organometallic cation, carbonium cation, tripium cation, oxonium cation, sulfonium cation, phosphonium cation and ammonium cation. More specifically, there can be mentioned triphenylcarbenium cation, tributylammonium cation, N,N-dimethylammonium cation and ferrocenium cation.

Of these, preferred are ionic compounds containing a boron compound as anion. More specifically, examples of trialkyl-substituted ammonium salts include triethylammoniumtetra(phenyl)boron, tripropylammoniumtetra (phenyl) boron, tri (n-butyl) ammoniumtetra (phenyl)boron, trimethylammoniumtetra(p-tolyl)boron, trimethylammoniumtetra(o-tolyl)boron, tributylammoniumtetra(pentafluorophenyl)boron, tripropylammoniumtetra(o,p-dimethylphenyl)boron, t ributylammoniumtetra(m,m-dimethylphenyl)boron, tributylammoniumtetra (p-trifluoromethylphenyl)boron, tri(n-butyl) ammoniumtetra (o-tolyl)boron and tri(n-butyl) ammoniumtetra(4-fluorophenyl)boron.

Examples of N,N-dialkylanilinium salts include N,N-dimethylaniliniumtetra(phenyl)boron, N,N-diethylaniliniumtetra(phenyl)boron and N,N-2,4,6-pentamethylaniliniumtetra(phenyl)boron.

Examples of dialkylammonium salts include di(n-propyl) ammoniumtetra(pentafluorophenyl)boron and dicyclohexylammoniumtetra(phenyl)boron.

Examples of triarylphosphonium salts include triphenylphosphoniumtetra(phenyl)boron, tri (methylphenyl)phosphoniumtetra(phenyl) boron and tri (dimethylphenyl)phosphoniumtetra(phenyl)boron.

Also employable as the ionic compound containing a boron atom are triphenylcarbeniumtetrakis(pentafluorophenyl)borate, N,N-dimethylaniliniumtetrakis(pentafluorophenyl)borate and ferroceniumtetrakis(pentafluorophenyl)borate.

Further, the following compounds can be also employed. (in the ionic compounds enumerated below, the counter ion is tri(n-butyl)ammonium, but the counter ion is in no way limited thereto.)

That is, there can be mentioned salts of anion, for example, bis{tri(n-butyl)ammonium}nonaborate, bis{tri(n-butyl)ammonium}decaborate, bis{tri(n-butyl) ammonium}undecaborate, bis{tri(n-butyl) ammonium}dodecaborate, bis{tri(n-butyl) ammonium}decachlorodecaborate, bis{tri(n-butyl) ammonium}dodecachlorododecaborate, tri(n-butyl) ammonium-1-carbadecaborate, tri(n-butyl)ammonium-1-carbaundecaborate, tri(n-butyl)ammonium-1-carbadodecaborate, tri(n-butyl)ammonium-1-trimethylsilyl-1-carbadecaborate and tri(n-butyl)ammoniumbromo-1-carbadecaborate.

Moreover, borane compounds and carborane compounds can be also employed. These compounds are employed as the Lewis acid or the ionic compounds.

Examples of the borane compounds and the carborane compounds include:

borane and carborane complex compounds and salts of carborane anion, for example, decaborane(14), 7,8-dicarbaundecaborane(13), 2,7-dicarbaundecaborane (13), undecahydride-7,8-dimethyl-7,8-dicarbaundecaborane, dodecahydride-11-methyl-2,7-dicarbaundecaborane, tri(n-butyl)ammonium-6-carbadecaborate (14), tri (n-butyl) ammonium-6-carbadecaborate (12), tri (n-butyl) ammonium-7-carbaundecaborate (13), tri (n-butyl) ammonium-7,8-dicarbaundecaborate (12), tri (n-butyl) ammonium-2,9-dicarbaundecaborate(12), tri(n-butyl) ammoniumdodecahydride-8-methyl-7,9-dicarbaundecaborate, tri(n-butyl) ammoniumundecahydride-8-ethyl-7,9-dicarbaundecaborate, tri(n-butyl) ammoniumdecahydride-8-butyl-7,9-dicarbundecaborate, tri(n-butyl) ammoniumundecahydride-8-allyl-7,9-dicarbaundecaborate, tri(n-butyl) ammoniumundecahydride-9-trimethylsilyl-7,8-dicarbaundecaborate and tri(n-butyl) ammoniumundecahydride-4,6-dibromo-7-carbaundecaborate; and carborane and salts of carborane, for example, 4-carbanonaborane(14), 1,3-dicarbanonaborane(13), 6,9-dicarbadecaborane(14), dodecahydride-1-phenyl-1,3-dicarbanonaborane, dodecahydride-1-methyl-1,3-dicarbanonaborane and undecahydride-1,3-dimethyl-1,3-dicarbanonaborane.

Furthermore, the following compounds can be also employed. (In the ionic compounds enumerated below, the counter ion is tri(n-butyl)ammonium, but the counter ion is in no way limited thereto.

That is, there can be mentioned salts of metallic carborane and metallic borane anion, for example, tri(n-butyl) ammoniumbis(nonahydride-1,3-dicarbononaborate) cobaltate(III), tri(n-butyl)ammoniumbis(undecahydride-7,8-dicarbaundecaborate)ferrate(III), tri(n-butyl) ammoniumbis(undecahydride-7,8-dicarbaundecaborate) cobaltate(III), tri(n-butyl)ammoniumbis(undecahydride-7,8-dicarbaundecaborate)nickelate(III), tri(n-butyl) ammoniumbis (undecahydride-7,8-dicarbaundecaborate) cuprate (III), tri(n-butyl)ammoniumbis(undecahydride-7,8-dicarbaundecaborate)aurate(III), tri(n-butyl)ammoniumbis (nonahydride-7,8-dimethyl-7,8-dicarbaundecaborate)ferrate (III), tri(n-butyl)ammoniumbis(nonahydride-7,8-dimethyl-7,8-dicarbaundecaborate)chromate(III), tri(n-butyl) ammoniumbis(tribromooctahydride-7,8-dicarbaundecaborate)cobaltate(III), tri(n-butyl) ammoniumbis(dodecahydridedicarbadodecaborate) cobaltate(III), bis{tri(n-butyl ammonium bis} (dodecahydridedodecaborate)nickelate(III), tris{tri(n-butyl ammonium bis}(undecahydride-7-carbaundecaborate) chromate(III), bis{tri(n-butyl)ammonium bis} (undecahydride-7-carbaundecaborate)manganate(IV), bis{tri(n-butyl)ammonium bis}(undecahydride-7-carbaundecaborate)cobaltate(III) and bis{tri(n-butyl) ammonium bis}(undecahydride-7-carbaundecaborate) nickelate(IV).

The compounds (B-2) which react with the transition metal compound (A) to form an ion pair can be used in combination of two or more kinds.

The organoaluminum compound (C) (hereinafter sometimes referred to as "component (C)") used for the second olefin polymerization catalyst of the invention is, for example, an organoaluminum compound represented by the following formula (III):

$$R^9{}_nAlX_{3-n} \quad (III)$$

wherein $R^9$ is a hydrocarbon group of 1 to 12 carbon atoms, X is a halogen atom or a hydrogen atom, and n is 1 to 3.

In the above formula (III), $R^9$ is a hydrocarbon group of 1 to 12 carbon atoms, e.g., an alkyl group, a cycloalkyl group or an aryl group. Particular examples thereof include methyl, ethyl, n-propyl, isopropyl, isobutyl, pentyl, hexyl, octyl, cyctopentyl, cyclohexyl, phenyl and tolyl.

Examples of such organoaluminum compounds (C) include:

trialkylaluminums, such as trimethylaluminum, triethylaluminum, triisopropylaluminum, triisobutylaluminum, trioctylaluminum and tri(2-ethylhexyl)aluminum;

alkenylaluminums, such as isoprenylaluminum, dialkylaluminum halides, such as dimethylaluminum chloride, diethylaluminum chloride, diisopropylaluminum chloride, diisobutylaluminum chloride and dimethylaluminum bromide;

alkylaluminum sesquihalides, such as methylaluminum sesquichloride, ethylaluminum sesquichloride, isopropylaluminum sesquichloride, butylaluminum sesquichloride and ethylaluminum sesquibromide;

alkylaluminum dihalides, such as methylaluminum dichloride, ethylaluminum dichloride, isopropylaluminum dichloride and ethylaluminum dibromide; and alkylaluminum hydrides, such as diethylaluminum hydride and diisobutylaluminum hydride.

Also employable as the organoaluminum compound (C) is a compound represented by the following formula (IV):

$$R^9{}_n AlL_{3-n} \quad (III)$$

wherein $R^9$ is the same hydrocarbon as in the above formula (III); L is —$OR^{10}$ group, —$OSiR^{11}{}_3$group, —$OAlR^{12}{}_2$ group, —$NR^{13}{}_2$group, —$SiR^{14}{}_3$group or —$N(R^{15})AlR^{16}{}_2$ group; n is 1 to 2; $R^{10}$, $R^{11}$, $R^{12}$ and $R^{16}$ are each methyl, ethyl, isopropyl, isobutyl, cyclohexyl, phenyl or the like; $R^{13}$ is hydrogen, methyl, ethyl, isopropyl, phenyl, trimethylsilyl or the like; and $R^{14}$ and $R^{15}$ are each methyl, ethyl or the like.

Examples of such organoatuminum compounds (C) include:

(1) compounds represented by the formula $R^9{}_n Al(OR^{10})_{3-n}$, for example, dimethylaluminum methoxide, diethylaluminum ethoxide and diisobutylaluminum methoxide;

(2) compounds represented by the formula $R^9{}_n Al(OSiR^{11}{}_3)_{3-n}$, for example, $Et_2Al(OSiME_3)$, (iso-Bu)$_2$Al(OSiMe$_3$) and (iso-Bu)$_2$Al(OSiEt$_3$);

(3) compounds represented by the formula $R^9{}_n Al(OAlR^{12}{}_2)_{3-n}$, for example, $Et_2AlOlEt_2$ and (iso-Bu)$_2$AlOAl(iso-Bu)$_2$;

(4) compounds represented by the formula $R^9{}_n Al(NR^{13}{}_2)_{3-n}$, for example, Me$_2$AlNEt$_2$, Et$_2$AlNHMe, ME$_2$AlNHEt, Et$_2$AlN(SiMe$_3$)$_2$ and (iso-Bu)$_2$AlN(SiMe$_3$)$_2$;

(5) compounds represented by the formula $R^9{}_n Al(Sir^{14}{}_3)_{3-n}$, for example, (iso-Bu)$_2$AlSiMe$_3$; and (6) compounds represented by the formula $R^9{}_n (N(R^{15})AlR^{16}{}_2)_{3-n}$, for example, Et$_2$AlN(Me)AlEt$_2$ and (iso-Bu)$_2$AlN(Et)Al(iso-Bu)$_2$.

Of the organoaluminum compounds represented by the formulas (III) and (IV), the compounds represented by the formulas $R^9{}_3Al$, $R^9{}_nAl(OR^{10})_{3-n}$ and $R^9{}_nAl(OAlR^{12}{}_2)_{3-n}$ are preferred, and the compounds having these formulas wherein R is an isoalkyl group and n is 2 are particularly preferred.

In the present invention, water may be used as a catalyst component in addition to the component (A), the component (B-1), the component(B-2) and the component (C). As the water employable in the invention, there can be mentioned water dissolved in a polymerization solvent described later, and adsorbed water or water of crystallization contained in a compound or a salt used for preparing the component (B-1).

The first olefin polymerization catalyst of the invention can be prepared by mixing the component (A) and the component (B-1) (or the component (B-2)), and if desired water (as a catalyst component), in an inert hydrocarbon medium (solvent) or an olefin medium (solvent).

There is no specific limitation on the order of mixing those components, but it is preferred that the component (B-1) (or the component (B-2) is mixed with water, followed by mixing with the component (A).

The second olefin polymerization catalyst of the invention can be prepared by mixing the component (A), the component (B-1) (or the component (B-2)) and the component (C), and if desired water (as a catalyst component), in an inert hydrocarbon medium (solvent) or an olefin medium (solvent).

There is no specific limitation on the order of mixing those components. However, when the component (B-1) is used, it is preferred that the component (B-1) is mixed with the component (C), followed by mixing with the component (A). When the component (B-2) is used, it is preferred that the component (C) is mixed with the component (A), followed by mixing with the component (B-2).

In the mixing of each components, an atomic ratio (Al/transition metal) of aluminum in the component (B-1) to the transition metal in the component (A) is in the range of usually 10 to 10,000, preferably 20 to 5,000; and a concentration of the component (A) is in the range of about $10^{-8}$ to $10^{-1}$ mol/liter-medium, preferably $10^{-7}$ to $5 \times 10^{-2}$ mol/liter-medium.

When the component (B-2) is used, a molar ratio (component (A)/component (B-2)) of the component (A) to the component (B-2) is in the range of usually 0.01 to 10, preferably 0.1 to 5; and a concentration of the component (A) is in the range of about $10^{-8}$ to $10^{-1}$ mol/liter-medium, preferably $10^{-7}$ to $5 \times 10^{-2}$ mol/liter-medium.

In the preparation of the second olefin polymerization catalyst of the invention, an atomic ratio ($Al_c/Al_{B-1}$) of the aluminum atom ($Al_c$ in the component (C) to the aluminum atom ($Al_{B-1}$) in the component (B-1) is in the range of usually 0.02 to 20, preferably 0.2 to 10.

When water is used as a catalyst component, a molar ratio ($Al_{B-1}/H_2O$) of the aluminum atom ($Al_{B-1}$) in the component (B-1) to water ($H_2O$) is in the range of 0.5 to 50, preferably 1 to 40.

The above-mentioned each components may be mixed in a polymerizer, or a mixture of those components beforehand prepared may be fed to a polymerizer.

If the components are beforehand mixed, the mixing temperature is in the range of usually $-50°$ to $150°$ C., preferably $-20°$ to $120°$ C.; and the contact time is in the range of 1 to 1,000 minutes, preferably 5 to 600 minutes. The mixing temperature may be varied while the components are mixed and contacted with each other.

Examples of the media (solvents) used for preparing the olefin polymerization catalyst according to the invention include;

aliphatic hydrocarbons, such as propane, butane, pentane, hexane, heptane, octane, decane, dodecane and karosine;

alicyclic hydrocarbons, such as cyclopentane, cyclohexane and methylcyclopentane;

aromatic hydrocarbons, such as benzene, toluene and xylene;

halogenated hydrocarbons, such as ethylene chloride, chlorobenzene and dichcloromethane; and mixtures of these hydrocarbons.

Next, the third and the fourth olefin polymerization catalysts according to the invention are described.

The third olefin polymerization catalyst according to the invention comprises:

a fine particle carrier;

(A) a transition metal compound represented by the above formula (I); and (B) at least one compound selected from a group consisting of (B-1) an organoaluminum oxy-compound, and (B-2) an compound which reacts with the transition metal compound to form an ion pair;

said transition metal compound (A) and said at least one compound (B) being supported on the fine particle carrier.

The fourth olefin polymerization catalyst according to the invention comprises:

a solid catalyst component comprising:

a fine particle carrier, (A) a transition metal compound represented by the above formula (I), and (B) at least one compound selected from a group consisting of (B-1) an organoaluminum oxy-compound, and (B-2) an compound which reacts with the transition metal compound to form an ion pair, said transition metal compound (A) and said at least one compound (B) being supported on the fine particle carrier; and (C) an organoaluminum compound.

The transition metal compound (A) used for the third and the fourth olefin polymerization catalysts of the invention is the same as that for the aforesaid first and second olefin polymerization catalysts, and is represented by the above formula (I).

Examples of the organoaluminum oxy-compounds (B-1) used for the third and the fourth olefin polymerization catalysts of the invention are the same as those used for the first and the second olefin polymerization catalysts.

Examples of the compounds (B-2) which react with the transition metal compound (A) to form an ion pair and used for the third and the fourth olefin polymerization catalysts of the invention are the same as those used for the first and the second olefin polymerization catalysts.

Examples of the organoaluminum compounds (C) used for the fourth olefin polymerization catalyst of the invention are the same as those used for the second olefin polymerization catalyst.

The fine particle carrier used for the third and the fourth olefin polymerization catalysts of the invention is an inorganic or organic compound, and is a particulate or granular solid having a particle diameter of 10 to 300 μm, preferably 20 to 200 μm.

The inorganic carrier is preferably porous oxide, and examples thereof include $SiO_2$, $Al_2O_3$, $MgO$, $ZrO_2$, $TiO_2$, $B_2O_3$, $CaO$, $ZnO$, $BaO$, $ThO_2$, and mixtures thereof such as $SiO_2$—$MgO$, $SiO_2$—$Al_2O_3$, $SiO_2$—$TiO_2$, $SiO_2$—$V_2O_5$, $SiO_2$—$Cr_2O_3$ and $SiO_2$—$TiO_2$—$MgO$. Of these, preferred is a carrier containing $SiO_2$ and/or $Al_2O_3$ as its major component.

The above-mentioned inorganic oxides may contain carbonates, sulfates, nitrates and oxides, such as $Na_2CO_3$, $K_2CO_3$, $CaCO_3$, $MgCO_3$, $Na_2SO_4$, $Al_2(SO_4)_3$, $BaSO_4$, $KNO_3$, $Mg(NO_3)_2$, $Al(NO_3)_2$, $Na_2O$, $K_2$, and $Li_2O$, in a small amount.

The fine particle carrier is varied in its properties depending on the kind and the process for the preparation thereof, but preferably used in the invention is a carrier having a specific surface area of 50 to 1,000 m²/g, preferably 100 to 700 m²/g, and a pore volume of 0.3 to 2.5 cm³/g. The fine particle carrier is used after calcined at 100° to 1,000° C., preferably 150° to 700° C., if necessary.

Also employable as the fine particle carrier in the invention is a granular or particulate solid of an organic compound having a particle diameter of 10 to 300 μm. Examples of the organic compounds include (co)polymers prepared mainly from α-olefins of 2 to 14 carbon atoms such as ethylene, propylene, 1-butene and 4-methyl-1-pentene, and (co) polymers prepared mainly from vinylcyclohexene or styrene.

The fine particle carrier may contain a surface hydroxyl group or water. In this case, the surface hydroxyl group is contained in an amount of not less than 1.0% by weight, preferably 1.5 to 4.0% by weight, more preferably 2.0 to 3.5% by weight; and water is contained in an amount of not less than 1.0% by weight, preferably 1.2 to 20% by weight, more preferably 1.4 to 15% by weight. The water contained in the fine particle carrier means water which is adsorbed on the surface of the fine particle carrier.

The amount (% by weight) of the adsorbed water and the amount (% by weight) of the surface hydroxyl group in the fine particle carrier can be determined in the following manner.

Amount of adsorbed water

The weight reduction of the fine particle carrier after drying at 200° C. under ordinary pressure for 4 hours in a stream of nitrogen is measured, and a percentage of the weight after the drying to the weight before the drying is calculated.

Amount of Surface hydroxyl group

The weight of the fine particle carrier after drying at 200° C. under ordinary pressure for 4 hours in a stream of nitrogen is taken as X (g). The carrier is calcined at 1,000° C. for 20 hours to obtain a calcined product containing no surface hydroxyl group. The weight of the calcined product thus obtained is taken as Y (g). The amount (% by weight) of the surface hydroxyl group is calculated from the following formula.

Amount (wt. %) of surface hydroxyl group=${(X-Y)/X}\times100$

If a fine particle carrier having a specific amount of adsorbed water or a specific amount of surface hydroxyl group as described above is used, an olefin polymerization catalyst capable of preparing an olefin polymer having excellent particle properties and having high polymerization activities can be obtained.

Further, in the third and the fourth olefin polymerization catalysts of the invention, such water as described in the first and the second olefin polymerization catalysts may be used as a catalyst component.

The third olefin polymerization catalyst of the invention (i.e., solid catalyst component) can be prepared by mixing the fine particle carrier, the component (A) and the component (B-1) (or the component (B-2)), and if desired water (catalyst component), in an inert hydrocarbon medium (solvent) or an olefin medium (solvent). In the mixing of those components, the component (C) can be further added.

There is no specific limitation on the order of mixing those components.

However, preferred processes are:

a process in which the fine particle carrier is mixed and contacted with the component (B-1) (or the component (B-2), and then with the component (A), followed by mixing with water if desired;

a process in which a mixture of the component (B-1) (or the component (B-2)) and the component (A) is mixed and contacted with the fine particle carrier, followed by mixing with water if desired; and a process in which the fine particle carrier is mixed and contacted with the component (B-1) (or the component (B-2)) and water, followed by mixing with the component (A).

In the mixing of each components, the component (A) is used in an amount of usually $10^{-6}$ to $5 \times 10^{-3}$ mol, preferably $3 \times 10^{-6}$ to $10^{-3}$ mol, per 1 g of the fine particle carrier; and a concentration of the component (A) is in the range of about $5 \times 10^{-6}$ to $2 \times 10^{-2}$ mol/liter-medium, preferably $2 \times 10^{-5}$ to $10^{-2}$ mol/liter-medium. An atomic ratio (Al/transition metal) of aluminum in the component (B-1) to the transition metal in the component (A) is in the range of usually 10 to 3,000, preferably 20 to 2,000. When the component (B-2) is used, a molar ratio (component (A)/component (B-2)) of the component (A) to the component (B-2) is in the range of usually 0.01 to 10, preferably 0.1 to 5.

When water is used as a catalyst component, a molar ratio ($Al_{B-1}/H_2O$) of the aluminum atom ($Al_{B-1}$) in the component (B-1) to water ($H_2O$) is in the range of 0.5 to 50, preferably 1 to 40.

The temperature for mixing the components is in the range of usually $-50°$ to $150°$ C., preferably $-20°$ to $120°$ C.; and the contact time is in the range of 1 to 1,000 minutes, preferably 5 to 600 minutes. The mixing temperature may be varied while the components are mixed and contacted with each other.

The fourth olefin polymerization catalyst according to the invention is formed from the above-mentioned third olefin polymerization catalyst (solid catalyst component) and the organoaluminum compound (C). The component (C) is used in an amount of not more than 500 mol, preferably 5 to 200 mol, per 1 g of the transition metal atom in the component (A) contained in the solid catalyst component.

The third and the fourth olefin polymerization catalysts of the invention may contain other components useful for the olefin polymerization than the above-described components.

Examples of the inert hydrocarbon media (solvents) used for preparing the third and the fourth olefin polymerization catalysts of the invention are the same as those used for the first and the second olefin polymerization catalysts.

Next, the fifth and the sixth olefin polymerization catalysts according to the invention are described.

The fifth olefin polymerization catalyst according to the invention comprises:

a fine particle carrier;
(A) a transition metal compound represented by the above formula (I);
(B) at least one compound selected from a group consisting of
  (B-1) an organoaluminum oxy-compound, and
  (B-2) an compound which reacts with the transition metal compound to form an ion pair; and
a prepolymerized olefin polymer produced by prepolymerization.

The sixth olefin polymerization catalyst according to the invention comprises:

a fine particle carrier;
(A) a transition metal compound represented by the above formula (I);
(B) at least one compound selected from a group consisting of
  (B-1) an organoaluminum oxy-compound, and
  (B-2) an compound which reacts with the transition metal compound to form an ion pair;
(C) an organoaluminum compound; and
a prepolymerized olefin polymer produced by prepolymerization.

Examples of the fine particle carrier used for the fifth and the sixth olefin polymerization catalysts of the invention are the same as those for the aforesaid third and fourth olefin polymerization catalysts.

The transition metal compound (A) used for the fifth and the sixth olefin polymerization catalysts of the invention is the same as that for the aforesaid first and second olefin polymerization catalysts, and is represented by the above formula (I).

Examples of the organoaluminum oxy-compounds (B-1) used for the fifth and the sixth olefin polymerization catalysts of the invention are the same as those used for the first and the second olefin polymerization catalysts.

Examples of the compounds (B-2) which react with the transition metal compound (A) to form an ion pair and used for the fifth and the sixth olefin polymerization catalysts of the invention are the same as those used for the first and the second olefin polymerization catalysts.

Examples of the organoaluminum compounds (C) used for the sixth olefin polymerization catalyst of the invention are the same as those used for the second olefin polymerization catalyst.

Further, in the fifth and the sixth olefin polymerization catalysts of the invention, such water as described in the first and the second olefin polymerization catalysts may be used as a catalyst component.

The fifth olefin polymerization catalyst of the invention can be prepared by prepolymerizing a small amount of an olefin to the solid catalyst component. The solid catalyst component is obtained by mixing the fine particle carrier, the component (A) and the component (B-1) (or the component (B-2)), and if desired water, in an inert hydrocarbon medium (solvent) or an olefin medium (solvent). In the mixing of those components, the component (C) can be further added.

There is no specific limitation on the order of mixing those components.

However, preferred processes are:

a process in which the fine particle carrier is mixed and contacted with the component (B-1) (or the component (B-2)), and then with the component (A), followed by mixing with water if desired a process in which a mixture of the component (B-1) (or the component (B-2)) and the component (A) is mixed and contacted with the fine particle carrier, followed by mixing with water if desired; and a process in which the fine particle carrier is mixed and contacted with the component (B-1) (or the component (B-2)) and water, followed by mixing with the component (A).

The mixing of the components is desirably carried out with stirring.

In the mixing of each components, the component (A) is used in an amount of usually $10^{-6}$ to $5 \times 10^{-3}$ mol, preferably $3 \times 10^{-6}$ to $10^{-3}$ mol, per 1 g of the fine particle carrier; and a concentration of the component (A) is in the range of about $5 \times 10^{-6}$ to $2 \times 10^{-2}$ mol/liter-medium, preferably $10^{-5}$ to $10^{-2}$ mol/liter-medium. An atomic ratio (Al/transition metal) of aluminum in the component (B-1) to the transition metal in the component (A) is in the range of usually 10 to 3,000, preferably 20 to 2,000. When the component (B-2) is used, a molar ratio (component (A)/component (B-2)) of the component (A) to the component (B-2) is in the range of usually 0.01 to 10, preferably 0.1 to 5.

When water is used as a catalyst component, a molar ratio ($Al_{B-1}/H_2O$) of the aluminum atom ($Al_{B-1}$) in the component (B-1) to water ($H_2O$) is in the range of 0.5 to 50, preferably 1 to 40.

The temperature for mixing the components is in the range of usually −50° to 150° C., preferably −20° to 120° C.; and the contact time is in the range of 1 to 1,000 minutes, preferably 5 to 600 minutes. The mixing temperature may be varied while the components are mixed and contacted with each other.

The fifth olefin polymerization catalyst of the invention can be prepared by prepolymerizing an olefin in the presence of the above-mentioned components. The prepolymerization can be carried out by introducing an olefin into an inert hydrocarbon medium (solvent) in the presence of the components and if necessary the component (C).

In the prepolymerization, the component (A) is used in an amount of usually $10^{-5}$ to $2 \times 10^{-2}$ mol/liter, preferably $5 \times 10^{-5}$ to $10^{-2}$ mol/liter. The prepolymerization temperature is in the range of −20° to 80° C., preferably 0° to 50° C.; and the prepolymerization time is 0.5 to 100 hours, preferably about 1 to 50 hours.

The olefin used for the prepolymerization is selected from olefins which are used for polymerization, and it is preferable to use the same monomer as used in the polymerization or a mixture of the same monomer as used in the polymerization and an α-olefin.

In the olefin polymerization catalyst of the invention obtained as above, it is desired that the transition metal atom is supported in an amount of about $10^{-6}$ to $10^{-3}$ g.atom, preferably $2 \times 10^{-6}$ to $3 \times 10^{-4}$ g.atom, per 1 g of the fine particle carrier; and the aluminum atom is supported in an amount of about $10^{-3}$ to $10^{-1}$ g.atom, preferably $2 \times 10^{-3}$ to $5 \times 10^{-2}$ g.atom, per 1 g of the fine particle carrier. Further, it is also desired that the component (B-2) is supported in an amount of $5 \times 10^{-7}$ to 0.1 g.atom, preferably $2 \times 10^{-7}$ to $3 \times 10^{-2}$ g.atom, in terms of the boron atom contained in the component (B-2).

The amount of the prepolymerized polymer prepared by the prepolymerization is desired to be in the range of about 0.1 to 500 g, preferably 0.3 to 300 g, particularly preferably 1 to 100 g, per 1 g of the fine particle carrier.

The sixth olefin polymerization catalyst of the invention is formed from the above-mentioned fifth olefin polymerization catalyst (component) and the organoaluminum compound (C). The organoaluminum compound (C) is used in an amount of not more than 500 mol, preferably 5 to 200 mol, per 1 g.atom of the transition metal atom in the component (A).

The fifth and the sixth olefin polymerization catalysts of the invention may contain other components useful for the olefin polymerization than the above-described components.

Examples of the inert hydrocarbon solvents used for the fifth and the sixth olefin polymerization catalysts of the invention are the same as those used for preparing the aforesaid first and second olefin polymerization catalysts.

Polyolefins obtained by the use of the olefin polymerization catalysts as described above have a narrow molecular weight distribution, a narrow composition distribution and a high molecular weight and the olefin polymerization catalysts have a high polymerization activity.

Further, when olefins of 3 or more carbon atoms are polymerized in the presence of the olefin polymerization catalysts, polyolefins having excellent stereoregularity can be obtained.

Next, the process for olefin polymerization according to the present invention is described.

An olefin is polymerized in the presence of any of the above-described olefin polymerization catalysts. The polymerization may be carried out by a liquid phase polymerization process such as a suspension polymerization or by a gas phase polymerization.

In the liquid phase polymerization process, the same inert hydrocarbon solvent as used in the preparation of the catalyst can be used, or the olefin itself can be also used as a solvent.

In the polymerization of an olefin using the first or the second polymerization catalyst, the catalyst is used in an amount of usually $10^{-8}$ to $10^{-3}$ g.atom/liter, preferably $10^{-7}$ to $10^{-4}$ g.atom/liter, in terms of a concentration of the transition metal atom of the component (A) in the polymerization system.

In the polymerization of an olefin using the third or the fourth polymerization catalyst, the catalyst is used in an amount of usually $10^{-8}$ to $10^{-3}$ g.atom/liter, preferably $10^{-7}$ to $10^{-4}$ g.atom/liter, in terms of a concentration of the transition metal atom of the component (A) in the polymerization system. In this case, an aluminoxane which is not supported on the carrier may be employed, desired.

In the polymerization of an olefin using the fifth or the sixth polymerization catalyst, the catalyst is used in an amount of usually $10^{-8}$ to $10^{-3}$ g.atom/liter, preferably $10^{-7}$ to $10^{-4}$ g.atom/liter, in terms of a concentration of the transition metal atom of the component (A) in the polymerization system. In this case, an aluminoxane which is not supported on the carrier may be employed, if desired.

In the slurry polymerization, the temperature for the olefin polymerization is in the range of usually −50° to 100° C., preferably 0° to 90° C. In the liquid phase polymerization, the temperature is in the range of usually 0° to 250° C., preferably 20° to 200° C. In the gas phase polymerization process, the temperature is in the range of usually 0° to 120° C., preferably 20° to 100° C. The polymerization pressure is in the range of usually atmospheric pressure to 100 kg/cm², preferably atmospheric pressure to 50 kg/cm². The polymerization reaction can be carried out either batchwise, semi-continuously or continuously. Further, the polymerization may be performed in two or more stages having different reaction conditions.

The molecular weight of the resulting olefin polymer can be regulated by allowing hydrogen to exist in the polymerization system or by varying the polymerization temperature.

Examples of the olefins to be polymerized using the olefin polymerization catalysts of the invention include:

α-olefins of 2 to 20 carbon atoms, such as ethylene, propylene, 1-butene, 1-pentene, 1-hexene, 4-methyl-1-pentene, 1-octene, 1-decene, 1-tetradecene, 1-hexadecene, 1-octadecene and 1-eicosene; and cycloolefins of 3 to 20 carbon atoms, such as cyclopentene, cycloheptene, norbornene, 5-methyl-2-norbornene, tetracyclododecene and 2-methyl-1,4,5,8-dimethano-1,2,3,4,4a,5,8,8a-octahydronaphthalene.

Also employable are styrene, vinylcyclohexane, diene, etc.

When the olefin polymerization catalyst of the invention is used to polymerize an α-olefin of 3 or more carbon atoms, obtainable is a polymer having a lower melting point as compared with a polymer obtained by using a conventional metallocene type catalyst, even though the polymers have the almost the same molecular weight. Further, when the catalyst of the invention is used, a copolymer having a low melting point can be obtained even if the amount of recurring units derived from a comonomer is small.

If an α-olefin of 3 or more carbon atoms is polymerized using the olefin polymerization catalyst of the invention, a great number of inversely inserted monomer units are present in the molecules of the resultant olefin polymer. It is known that in the α-olefin prepared by a polymerization of an α-olefin of 3 or more carbon atoms in the presence of a chiral metallocene catalyst, 2,1-insertion or 1,3-insertion takes place in addition to the ordinary 1,2-insertion, whereby an inversely inserted unit such as a 2,1-insertion or 1,3-insertion is formed in the olefin polymer molecule (see: Makromol. Chem., Rapid Commun., 8,305 (1987), by K. Soga, T. Shiono, S. Takemura and W. Kaminsky). It is also known that when inverse insertions are present in the olefin polymer molecule, the melting point of the olefin polymer becomes low for its stereoregularity (see: Polymer, 30, 1350 (1989), by T. Tsutsui, N. Ishimura, A. Mizuno, A. Toyota and N. Kashiwa).

In the molecule of the olefin polymer obtained by polymerizing an α-olefin of 3 or more carbon atoms using the olefin polymerization catalyst of the invention, a great number of inversely inserted monomer units are present, and hence it is presumed that the melting point of the olefin polymer is lower than the melting point of an olefin polymer having almost the same molecular weight which is obtained by the use of a conventional catalyst.

The propylene polymer, the propylene copolymer and the propylene elastomer according to the invention are described hereinafter.

Propylene polymer

The propylene polymer of the invention is a polymer comprising propylene units, but it may contain constituent units derived from other olefins than propylene in an amount of less than 0.5% by mol, preferably less than 0.3% by mol, more preferably less than 0.1% by mol.

The propylene polymer of the invention has a triad tacticity of not less than 90%, preferably not less than 93%, more preferably not less than 95%. The term "triad tacticity" means a proportion of such chains of three propylene units (i.e., chains consisting of three propylene units continuously bonded that the directions of methyl branches in the propylene chain are the same as each other and each propylene units are bonded to each other with head-to-tail bonds, to total three propylene units-chains in the polymer, and this term is sometimes referred to as "mm fraction" hereinafter.

The triad tacticity can be determined from a $^{13}$C-NMR spectrum of the propylene polymer.

120° C. to measure the $^{13}$C-NMR spectrum. The measurement is conducted under the conditions of a flip angle of 45° and a pulse interval of not less than 3.4 $T_1$ ($T_1$ is a maximum value with respect to a spin-lattice relaxation time of the methyl group). $T_1$ of the methylene group and $T_1$ of the methine group are each shorter than that of the methyl group, and hence the magnetization recovery of all carbons under these conditions is not less than 99%.

With respect to the chemical shift, the methyl group of the third unit in the 5 propylene units-chain consisting of head-to-tail bonds and having the same directions of the methyl branches is set to 21.593 ppm, and the chemical shift of other carbon peak is determined by using the above-mentioned value as a reference. Accordingly, a peak based on the methyl group of the second unit in the three propylene units-chain having PPP(mm) structure appears in the range of 21.1 to 21.8 ppm; a peak based on the methyl group of the second unit in the three propylene units-chain having PPP(mr) structure appears in the range of 20.2 to 21.1 ppm; and a peak based on the methyl group of the second unit in the three propylene units-chain having PPP(rr) structure appears in the range of 19.4 to 20.2 ppm.

PPP(mm), PPP(mr) and PPP(rr) have the following 3 propylene units-chain structure with head-to-tail bonds, respectively.

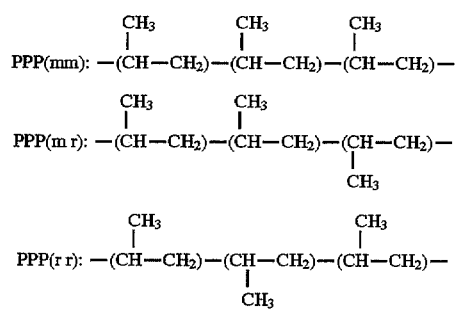

In addition to the ordered structures represented by the above-described PPP(mm), PPP(mr) and PPP(rr), the propylene polymer has a structure (i) containing an inversely inserted unit based on the 2,1-insertion and a structure (ii) containing an inversely inserted unit based on the 1,3-insertion, in small amounts.

Structure (i)

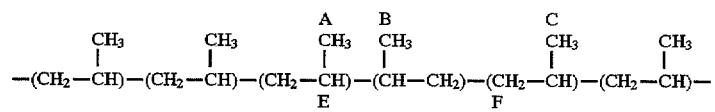

Structure (ii)

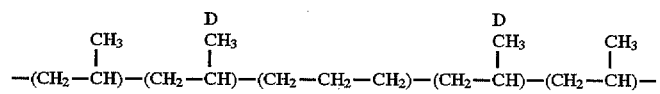

The $^{13}$C-NMR spectrum is measured in the following manner. A sample of 50 to 60 mg is completely dissolved in a mixed solvent containing about 0.5 ml of hexachlorobutadiene, o-dichlorobenzene or 1,2,4-trichlorobenzene and about 0.05 ml of deuterated benzene (i.e., lock solvent) in a NMR sample tube (diameter: 5 mm), and then subjected to a proton perfect decoupling method at The aforementioned definition of the mm fraction is not applied to the propylene units having the carbons attached with marks A, B, C and D among the carbons attached with marks A to F. The carbon A and the carbon B resonate in the region of 16.5 to 17.5 ppm, the carbon C resonates in the vicinity of 20.8 ppm (mr region), and the carbon D resonates in the vicinity of 20.7 ppm (mr region). In the structure (i)

and the structure (ii), however, not only the peak of the methyl group but also the peaks of the adjacent methylene and methine groups must be confirmed.

In the structure (ii), $-(CH_2)_3-$ unit is produced and a unit corresponding to one methyl group disappears as a result of hydrogen transfer polymerization.

Accordingly, the mm fraction in all of the polymer chains can be represented by the following formula:

$$\text{mm Fraction (\%)} = \frac{\text{area of methyl group (21.1~21.8 ppm)}}{\Sigma I_{CH_3} + (I_{\alpha\delta} + I_{\beta\gamma})/4} \times 100$$

wherein $\Sigma ICH_3$ denotes the total areas of all peaks derived from the methyl groups.

Further, $I_{\alpha\delta}$ and $I_{\beta\gamma}$ are an area of αγ peak (resonance in the vicinity of 37.1 ppm) and an area of βγ peak (resonance in the vicinity 27.3 ppm), respectively. Naming of these methylene peaks was made in accordance with a method by Carman, et al. (Rubber Chem. Tachnol., 44 (1971), 781).

In the polymerization to prepare a propylene polymer, the 1,2-insertion of the propylene monomer mainly takes place, but the 2,1-insertion or the 1,3-insertion thereof sometimes takes place. The 2,1-insertion forms the inversely inserted unit represented by the aforementioned structure (i) in the polymer chain. The proportion of the 2,1-propylene monomer insertions to the all propylene insertions was calculated by the following formula.

Proportion of inversely inserted units based on 2,1-insertion (%) =

$$0.5 \times \frac{\text{(area of methyl group (16.5~17.5 ppm)}}{\Sigma I_{CH_3} + (I_{\alpha\delta} + I_{\beta\gamma})/4} \times 100$$

Likewise, the proportion of the 1,3-propylene monomer insertions represented by the aforementioned structure (ii) to the all propylene insertions was calculated by the following formula.

Proportion of inversely inserted units based on 3,1-insertion (%) =

$$\frac{(I_\alpha\delta + I_{\beta\eta})/4}{\Sigma I_{CH_3} + (I_{\alpha\delta} + I_{\beta\gamma})/4} \times 100$$

In the propylene polymer according to the invention, the proportion of the inversely inserted units based on the 2,1-insertion in all propylene insertions, as measured by $^{13}$C-NMR, is not less than 0.7%, preferably 0.7 to 2.0%. Further, in the propylene polymer of the invention, the proportion of the inversely inserted units based on the 1,3-insertion in all propylene insertions is not more than 0.05%, preferably not more than 0.04%, more preferably not more than 0.03%.

The propylene polymer of the invention has an intrinsic viscosity [η], as measured in decahydronaphthalene at 135° C., of 0.1 to 12 dl/g, preferably 0.5 to 12 dl/g, more preferably 1 to 12 dl/g.

The propylene polymer of the invention can be prepared by polymerizing propylene in the presence of, for example, the aforesaid olefin polymerization catalysts. The polymerization can be carried out by a liquid phase polymerization (e.g., a suspension polymerization and a solution polymerization) or a gas phase polymerization.

In the liquid phase polymerization, the same inert hydrocarbon solvent as used for preparing the aforesaid catalyst can be used, or propylene can be also used as a solvent.

In the suspension polymerization, the temperature for polymerizing propylene is in the range of usually −50° to 100° C., preferably 0° to 90° C. In the solution polymerization, the temperature is in the range of usually 0° to 250° C., preferably 20° to 200° C. In the gas phase polymerization, the temperature is in the range of usually 0° to 120° C., preferably 20° to 100° C. The polymerization pressure is in the range of usually atmospheric pressure to 100 kg/cm$^2$, preferably atmospheric pressure to 50 kg/cm$^2$. The polymerization reaction can be carried out either batchwise, semicontinuously or continuously. Further, the polymerization can be carried out in two or more stages having different reaction conditions.

The molecular weight of the resultant propylene polymer can be regulated by allowing hydrogen to exist in the polymerization system or by varying the polymerization temperature and the polymerization pressure.

Propylene copolymer

The propylene copolymer of the invention is a propylene/ethylene random copolymer containing propylene units in an amount of 95 to 99.5% by mol, preferably 95 to 99% by mol, more preferably 95 to 98% by mol, and containing ethylene units in an amount of 0.5 to 5% by mol, preferably 1 to 5% by mol, more preferably 2 to 5% by mol.

Such propylene copolymer may contain constituent units derived from other olefins than propylene and ethylene in an amount of not more than 5% by mol.

In the propylene copolymer of the invention, the triad tacticity of the propylene unit chain consisting of head-to-tail bonds, as measured by $^{13}$C-NMR, is not less than 90% preferably not less than 93%, more preferably not less than 96%.

The triad tacticity (mm fraction) of the propylene copolymer can be determined from a $^{13}$C-NMR spectrum of the propylene copolymer and the following formula:

$$\text{mm Fraction} = \frac{PPP(mm)}{PPP(mm) + PPP(mr) + PPP(rr)}$$

wherein PPP(mm); PPP(mr) and PPP(rr) denote peak areas derived from the methyl groups of the second units in the following three propylene units-chains consisting of head-to-tail bonds, respectively:

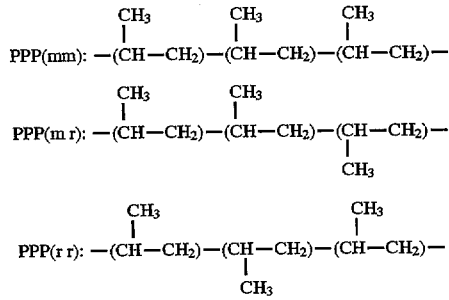

The $^{13}$C-NMR spectrum of the propylene copolymer can be measured in the same manner as described for the propylene polymer. The spectrum relating to the methyl carbon region (16–23 ppm) can be classified into the first region (21.1–21.9 ppm), the second region (20.3–21.0 ppm), the third region (19.5–20.3 ppm) and the fourth region (16.5–17.5 ppm). Each peak in the spectrum was assigned with reference to a literature "Polymer", 30 (1989) 1350.

In the first region, the methyl group of the second unit in the three propylene units-chain represented by PPP(mm) resonates.

In the second region, the methyl group of the second unit in the three propylene units-chain represented by PPP(mr)

resonates and the methyl group (PPE-methyl group) of a propylene unit whose adjacent units are a propylene unit and an ethylene unit resonates (in the vicinity of 20.7 ppm).

In the third region, the methyl group of the second unit in the three propylene units-chain represented by PPP(rr) resonates and the methyl group (EPE-methyl group) of a propylene unit whose adjacent units are ethylene units resonate (in the vicinity of 19.8 ppm).

Further, the propylene copolymer has the following structures (i) and (iii) containing an inversely inserted unit.

Structure (i)

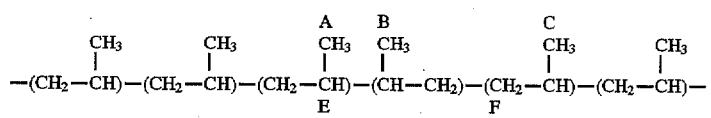

Structure (iii)

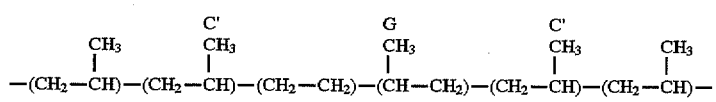

Of the carbons attached with marks A to G, a peak of the carbon C and a peak of the carbon C' appear in the second region, a peak of the carbon G appears in the third region, and a peak of the carbon A and a peak of the carbon B appear in the fourth region.

Of the peaks which appear in the first to fourth regions as described above, peaks which are not based on the three propylene units-chain consisting of head-to-tail bonds are peaks based on the PPE-methyl group, the EPE-methyl group, the carbon C, the carbon C', the carbon G, the carbon A and the carbon B.

The peak area based on the PPE-methyl group can be evaluated by the peak area of the PPE-methine group (resonance in the vicinity of 30.6 ppm), and the peak area based on the EPE-methyl group can be evaluated by the peak area of the EPE-methine group (resonance in the vicinity of 32.9 ppm). The peak area based on the carbon C can be evaluated by ½ as much as the sum of the peak areas of the carbon F and the carbon E both having the inversely inserted structure (structure (i)) (resonance in the vicinity of 35.6 ppm and resonance in the vicinity of 35.4 ppm, respectively). The peak area based on the carbon C' can be evaluated by ½ as much as the sum of the peak areas of the αβ methylene carbons having the inversely inserted structure (structure (iii)) (resonance in the vicinity of 34.3 ppm and resonance in the vicinity of 34.5 ppm, respectively). The peak area based on the carbon G can be evaluated by the peak area of the adjacent methine carbon (resonance in the vicinity of 33.7 ppm).

Accordingly, by subtracting these peak areas from the total peak areas of the second region and the third region, the peak areas based on the three propylene units-chains (PPP (mr) and PPP(rr) consisting of head-to-tail bonds can be obtained.

Since the positions of the carbon A peak and the carbon B peak have no concern with the peak of the three propylene units-chain (PPP), they do not need to be taken into account.

Thus, the peak areas of PPP(mm), PPP(mr) and PPP(rr) can be evaluated, and hence the triad tacticity of the propylene unit chain consisting of head-to tail bonds can be determined.

In the propylene copolymer of the invention, the proportion of the inversely inserted units based on the 2,1-insertion in all propylene insertions, as measured by $^{13}$C-NMR, is not less than 0.5%, preferably 0.5 to 1.5%. Further, in the propylene copolymer of the invention, the proportion of the inversely inserted units based on the 1,3-insertion of the propylene monomer in all propylene insertions is not more than 0.05%, preferably not more than 0.04%, more preferably not more than 0.03%.

In the polymerization, the 1,2-insertion of the propylene monomer (i.e., the methylene side is bonded to the catalyst) mainly takes place, but the 2,1-insertion thereof sometimes takes place. The 2,1-insertion forms the inversely inserted unit in the polymer.

The proportion of the 2,1-insertions to the all propylene insertions in the propylene copolymer was calculated by the following formula with reference to "Polymer", 30 1989) 1350.

Proportion of inversely inserted unit based on 2,1-insertion (%) =

$$\frac{0.5\, I\alpha\beta\, (\text{sturcture (i)}) + 0.25\, I\alpha\beta\, (\text{structure (iii)})}{I\alpha\alpha + I\alpha\beta\, (\text{sturcture (i)}) + 0.5\, \{I\alpha\gamma + I\alpha\beta\, (\text{structure (iii)}) + I\alpha\delta\}} \times 100$$

Naming of the peaks in the above formula was made in accordance with a method by Carman, et al. (Rubber Chem. Tachnol., 44 (1971), 781). $I_{\alpha\delta}$ denotes a peak area of the αδ peak.

The proportion (%) of the amount of the three propylene units-chains based on the 1,3-insertion was determined by dividing ½ as much as the area of the βγ peak (resonance in the vicinity of 27.4 ppm) by the sum of all the methyl group peaks and ½ as much as the βγ peak, and then multiplying the resulting value by 100.

The propylene copolymer of the invention has an intrinsic viscosity [η], as measured in decahydronaphthalene at 135° C., of 0.1 to 12 dl/g, preferably 0.5 to 12 dl/g, more preferably 1 to 12 dl/g.

The propylene copolymer of the invention can be prepared by copolymerizing propylene and ethylene in the presence of, for example, the aforesaid olefin polymerization catalysts. The copolymerization can be carried out by a liquid phase polymerization (e.g., a suspension polymerization and a solution polymerization) or a gas phase polymerization.

In the liquid phase polymerization, the same inert hydrocarbon solvent as used for preparing the aforesaid catalyst can be used, and propylene and/or ethylene can be also used as a solvent.

In the suspension polymerization, the temperature for copolymerizing propylene and ethylene is in the range of usually −50° to 100° C., preferably 0° to 90° C. In the solution polymerization, the temperature is in the range of usually 0° to 250° C., preferably 20° to 200° C. In the gas phase polymerization, the temperature is in the range of usually 0° to 120° C., preferably 20° to 100° C. The copolymerization pressure is in the range of usually atmospheric pressure to 100 kg/cm², preferably atmospheric pressure to 50 kg/cm². The copolymerization reaction can be carried out either batchwise, semicontinuously or continuously. Further, the copolymerization can be carried out in two or more stages having different reaction conditions.

The molecular weight of the resultant propylene copolymer can be regulated by allowing hydrogen to exist in the copolymerization system or by varying the copolymerization temperature and the copolymerization pressure.

resonates and the methyl group (PPE-methyl group) of a propylene unit whose adjacent units are a propylene unit and an ethylene unit resonates (in the vicinity of 20.7 ppm).

In the third region, the methyl group of the second unit in the three propylene units-chain represented by PPP(rr) resonates and the methyl group (EPE-methyl group) of a propylene unit whose adjacent units are ethylene units resonates (in the vicinity of 19.8 ppm).

Further, the propylene elastomer has the following structures (iii) and (iv) containing an inversely inserted unit.

Structure (iii)

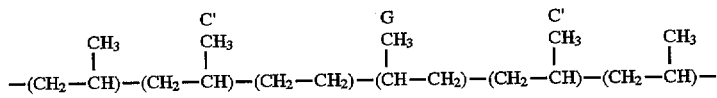

Structure (iv)

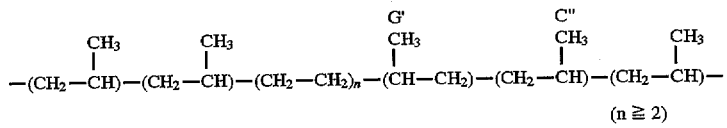

$(n \geq 2)$

Propylene elastomer

The propylene elastomer of the invention is a propylene/ethylene random copolymer containing propylene units in an amount of 50 to 95% by mol, preferably 60 to 93% by mol, more preferably 70 to 90% by mol, and containing ethylene units in an amount of 5 to 50% by mol, preferably 7 to 40% by mol, more preferably 10 to 30% by mol.

Such propylene elastomer may contain constituent units derived from other olefins than propylene and ethylene in an amount of not more than 10% by mol.

In the propylene elastomer of the invention, the triad tacticity of the propylene unit chain consisting of head-to-tail bonds, as measured by ¹³C-NMR, is not less than 90.0%, preferably not less than 92.0%, more preferably not less than 95.0%.

The triad tacticity (mm fraction) of the propylene elastomer can be determined from a ¹³C-NMR spectrum of the propylene elasmomer and the following formula:

$$\text{mm Fraction} = \frac{PPP(mm)}{PPP(mm) + PPP(mr) + PPP(rr)}$$

wherein PPP (ram), PPP (mr) and PPP (rr) have the same meanings as defined before.

The ¹³C-NMR spectrum of the propylene elastomer can be measured in the same manner as described for the propylene polymer. The spectrum relating to the methyl carbon region (19–23 ppm) can be classified into the first region (21.2–21.9 ppm), the second region (20.3–21.0 ppm) and the third region (19.5–20.3 ppm). Each peak in the spectrum was assigned with reference to a literature "Polymer", 30 (1989) 1350.

In the first region, the methyl group of the second unit in the three propylene units-chain represented by PPP(mm) resonates.

In the second region, the methyl group of the second unit in the three propylene units-chain represented by PPP(mr)

Of the carbons attached with marks C and G, a peak of the carbon C' and a peak of the carbon C" appear in the second region, and a peak of the carbon G and a peak of the carbon G' appear in the third region.

Of the peaks which appear in the first to third regions as described above, peaks which are not based on the 3 propylene units-chain consisting of head-to-tail bonds are peaks based on the PPE-methyl group, the EPE-methyl group, the carbon C', the carbon C", the carbon G and the carbon G'.

The peak area based on the PPE-methyl group can be evaluated by the peak area of the PPE-methine group (resonance in the vicinity of 30.6 ppm), and the peak area based on the EPE-methyl group can be evaluated by the peak area of the EPE-methine group (resonance in the vicinity of 32.9 ppm). The peak area based on the carbon C' can be evaluated by twice as much as the peak area of the methine carbon (resonance in the vicinity of 33.6 ppm) to which the methyl group of the carbon G is directly bonded; and the peak area based on the carbon C" can be evaluated by the peak area of the adjacent methine carbon (resonance in the vicinity of 33.2 ppm) of the methyl group of the carbon G'. The peak area based on the carbon G can be evaluated by the peak area of the adjacent methine carbon (resonance in the vicinity of 33.6 ppm); and the peak area based on the carbon G' can be also evaluated by the adjacent methine carbon (resonance in the vicinity of 33.2 ppm).

Accordingly, by subtracting these peak areas from the total peak areas of the second region and the third region, the peak areas based on the 3 propylene units-chains (PPP(mr) and PPP(rr)) consisting of head-to-tail bonds can be obtained.

Thus, the peak areas of PPP(mm), PPP(mr) and PPP(rr) can be evaluated, and hence the triad tacticity of the propylene unit chain consisting of head-to tail bonds can be determined.

In the propylene elastomer of the invention, the proportion of the inversely inserted units based on the 2,1-insertion in all propylene insertions, as measured by ¹³C-NMR, is not less than 0.5%, preferably 0.5 to 2.0%, more preferably 0.5 to 1.5%. Further, in the propylene elastomer of the invention, the proportion of the inversely inserted units based on the 1,3-insertion is not more than 0.05%, preferably not more than 0.03%.

The proportion of the 2,1-insertions to all of the propylene insertions in the propylene elastomer was calculated by the following formula with reference to "Polymer", 30 (1989) 1350.

Proportion of inversely inserted unit based on 2,1-insertion (%) =

$$\frac{0.25\, I\alpha\beta\,(\text{sturcture (iii)}) + 0.5\, I\alpha\beta\,(\text{structure (iv)})}{I\alpha\alpha + I\alpha\beta\,(\text{sturcture (iv)}) + 0.5\,\{I\alpha\gamma + I\alpha\beta\,(\text{structure (iii)}) + I\alpha\delta\}} \times 100$$

Naming of the peaks in the above formula was made in accordance with a method by Carman, et al. (Rubber Chem. Tachnol., 44 (1971), 781). $I_{\alpha\delta}$ denotes a peak area of the $\alpha\delta$ peak.

If it is difficult to determine the peak area of or the like directly from the spectrum because of overlapping of the peaks, a carbon peak having the corresponding area can be substituted therefor.

The proportion (%) of the amount of the three propylene units-chains based on the 1,3-insertion was determined by dividing ½ as much as the area of the $\beta\gamma$ peak (resonance in the vicinity of 27.4 ppm) by the sum of all the methyl group peaks and ½ as much as the $\beta\gamma$ peak, and then multiplying the resulting value by 100.

The propylene elastomer of the invention has an intrinsic viscosity [η], as measured in decahydronaphthalene at 135° C., of 0.1 to 12 dl/g, preferably 0.5 to 12 dl/g, more preferably 1 to 12 dl/g.

The propylene elastomer of the invention can be prepared by copolymerizing propylene and ethylene in the presence of, for example, the aforesaid olefin polymerization catalysts. The copolymerization can be carried out by a liquid phase polymerization (e.g., a suspension polymerization and a solution polymerization) or a gas phase polymerization.

In the liquid phase polymerization, the same inert hydrocarbon solvent as used for preparing the aforesaid catalyst can be used, and propylene and/or ethylene can be also used as a solvent.

In the suspension polymerization, the temperature for copolymerizing propylene and ethylene is in the range of usually −50° to 100° C., preferably 0° to 90° C. In the solution polymerization, the temperature is in the range of usually 0° to 250° C., preferably 20° to 200° C. In the gas phase polymerization, the temperature is in the range of usually 0° to 120° C., preferably 20° to 100° C. The copolymerization pressure is in the range of usually atmospheric pressure to 100 kg/cm², preferably atmospheric pressure to 50 kg/cm². The copolymerization reaction can be carried out either batchwise, semicontlnuously or continuously. Further, the copolymerization can be carried out in two or more stages having different reaction conditions.

The molecular weight of the resultant propylene elastomer can be regulated by allowing hydrogen to exist in the copolymerization system or by varying the copolymerization temperature and the copolymerization pressure.

EFFECT OF THE INVENTION

The novel transition metal compound according to the invention can be used as an olefin polymerization catalyst component.

The olefin polymerization catalyst of the invention has high polymerization activity and polyolefins prepared by the use of the catalyst have a narrow molecular weight distribution and a narrow composition distribution. When an α-olefin of 3 or more carbon atoms is used, obtainable is a polymer having a lower melting point as compared with a polymer obtained by using a conventional metallocene catalyst even though the polymers have almost the same molecular weight.

By the use of the catalyst of the invention, a copolymer having a low melting point can be obtained even if the amount of recurring units derived from a comonomer is small. Further, because of a small amount of a solvent-soluble components, the resultant copolymer is excellent in various properties such as transparency, heat-sealing properties and anti-blocking properties. Moreover, the synthesis of polypropylene can be made with fewer reaction steps and is more economical, as compared with the synthesis using a conventional metallocene catalyst when polypropylene having almost the same molecular weight is produced.

When a copolymer elastomer mainly containing ethylene units and propylene units is prepared using the olefin polymerization catalyst of the invention, the resultant elastomer has a high molecular weight. Such copolymer elastomer has a high strength, and hence when used as a modifier, the elastomer exhibits excellent effects in the improvement of impact strength and hardness of polyolefins. When the copolymer elastomer is used to prepare a propylene block copolymer, the resultant copolymer is well-balanced between heat resistance, rigidity or transparency and impact strength because the molecular weight of the copolymer elastomer can be increased. Also in the preparation of polyethylene, the resultant polyethylene is excellent in mechanical strength such as impact strength, tensile strength and flexural strength for the same reason.

The propylene polymer of the invention is excellent in rigidity, heat resistance, surface hardness, glossiness, transparency and impact resistance. Hence, it can be suitably used for various industrial parts, containers, films, non-woven fabrics, stretched yarns, etc.

The propylene copolymer of the invention is excellent in transparency, rigidity, surface hardness, heat resistance, heat-sealing properties, anti-blocking properties, bleed resistance and impact resistance. Hence, it can be suitably used for films, sheets, containers, stretched yarns, nonwoven fabrics, etc.

The propylene elastomer of the invention is excellent in heat resistance, impact absorbing properties, transparency, heat-sealing properties and anti-blocking properties. Hence, it can be singly used for films, sheets, etc., and moreover it can be suitably used as a modifier of a thermoplastic resin.

EXAMPLE

The present invention is described in more detail with reference to the following examples, but it should be construed that the invention is in no way limited to those examples.

In the present invention, an intrinsic viscosity [η], a molecular weight distribution (Mw/Mn), a stereoregularity (mmmm), a proportion of inversely inserted units and a melting point (Tm) are measured by the following methods.

Further, in some examples, a melt flow rate (MFR), a flexural modulus (FR), a heat distortion temperature (HDT), a heat seal-starting temperature and a heat seal-starting temperature after heat treatment, an izod impact strength (IZ) and a film impact strength are measured by the following method.

Intrinsic viscosity [η]

The intrinsic viscosity [η] was measured in decahydronaphthalene at 135° C., and expressed by dl/g.

Molecular weight distribution (Mw/Mn)

The molecular weight distribution (Mw/Mn) was measured in the following manner using GPC-150C produced by Milipore Co.

A separation column of TSK-GNH-HT having a diameter of 72 mm and a length of 600 mm was used, and the column temperature was set to 140° C. A sample (concentration 0.1 by weight, amount: 500 microliters) was moved in the column at a rate of 1.0 ml/min using o-dichlorobenzene (available from Wako Junyaku Kogyo K.K.) as a mobile phase and 0.025% by weight of BHT Takeda Chemical Industries, Ltd.) as an antioxidant. A differential refractometer was used as a detector. With respect to standard polystyrenes, polystyrenes available from Toso Co., Ltd. were used for Mw <1,000 and Mw>4×10$^6$, and polystyrenes available from Pressure Chemical Co. were used for 1,000<Mw<4×10$^6$.

Stereoregularity (mm triad tacticity and mmmm pentad tacticity)

mm triad tacticity was measured as mentioned above.

mmmm pentad tacticity was measured as follows.

About 50 mg of a sample was completely dissolved in a mixed solvent containing 0.5 ml of o-dichlorobenzene (or hexachlorobutadiene) and 0.1 ml of deuterated benzene in a NMR sample tube (diameter: 5 mm) at about 120° C., and then a $^{13}$C-NMR spectrum was measured (nuclear species: $^{13}$C, mode: perfect proton decoupling, temperature: 120° C.) by a GX500 type NMR measuring apparatus produced by Japan Electron Optics Laboratory Co., Ltd.

On the $^{13}$C-NMR spectrum, an area of a peak having resonance in the lowest magnetic field (21.8 ppm according to A. Zambelli, P. Locatelli, G. Bajo and F. A. Bovey, "Macromolecules", 8, 687 (1975)) was divided by a total area of all peaks of the methyl groups, and the resultant value was taken as a mmmm pentad tacticity value.

Proportion of inversely inserted units

For each of the polymers obtained in Examples 3 and 4 and Comparative Example 1, the proportions of the inversely inserted units based on the 2,1-insertion and the 1,3-insertion of a propylene monomer present in the propylene chain of the polymer were determined from the $^{13}$C-NMR spectrum and the following formulas.

$$2,1\text{-insertion (\%)} = \frac{0.5\, I\alpha\beta}{I\alpha\alpha + I\alpha\beta} \times 100$$

$$1,3\text{-insertion (\%)} = \frac{0.5\, I\alpha\beta}{I\alpha\alpha + I\alpha\beta + I\alpha\delta} \times 100$$

wherein $I\alpha\alpha$ is the total area of the $\alpha\alpha$ carbon peaks (resonances in the vicinity of 42.0 ppm and 46.2 ppm), $I\alpha\beta$ is the total area of the $\alpha\beta$ carbon peaks (resonances in the vicinity of 30.2 ppm and 35.6 ppm), and $I\alpha\delta$ is an area of the $\alpha\delta$ carbon peak (resonance in the vicinity of 37.1 ppm). Naming of the peaks (e.g., $\alpha\alpha$) was made in accordance with the classification by Carman, et al. (C. J. Carman and C. E. Wilkes, Rubber Chem. Technol., 44, 781 (1971)).

The proportions of the inversely inserted units in other examples were measured by the method described before.

Melting point (Tm)

The melting point was determined from an endothermic curve given by heating about 5 mg of a sample charged in an aluminum pan to 200° C. at a rate of 10° C./min, keeping it at 200° C. for 5 minutes, then cooling it to room temperature at a rate of 20° C./min and heating it again at a rate of 10° C./min. The measurement was conducted using a DSC-7 type apparatus produced by Perkin Elmer Co.

Melt flow rate (MFR)

The MFR is measured in accordance with ASTM D 1238 under a load of 2.16 kg at 230° C.

Flexural modulus (FM)

The FM is measured in accordance with ASTM D 790 using a specimen of 12.7 mm (width)×6.4 mm (thickness) ×127 mm (length) prepared by injection molding at a resin temperature of 200° C. and a molding temperature of 40° C. at a distance between spuns of 100 mm and a rate of flexing of 2 mm/min.

Heat distortion temperature (HDT)

The HDT is measured in accordance with ASTM D 648 under a load of 4.6 kg/cm$^2$.

Heat seal-starting temperature and heat seal-starting temperature after heat treatment With respect to a T-die film having a width of 30 cm and a thickness of 50 μm prepared using a single screw extruder having a diameter of 30 mm under the conditions of a resin temperature of 210° C. (at a portion of dicer of extruder), a take-off speed of 3 m/min and a temperature of cooling roll of 25° C., heat seal of two films is carried out using a heat sealer by sealing at various seal for temperatures under the conditions of a heat seal pressure of 2 kg/cm$^2$, a seal time of 1 second and a width of 5 mm, to prepare a sealed film. The above-prepared sealed film was allowed to cool.

The heat seal-staring temperature is defined as a temperature of the heat sealer when the peeling resistance of the sealed film becomes 300 g/25 mm, under such conditions that the sealed film is peeled off at 23° C., a peeling speed of 200 mm/min and a peeling angle of 180°.

Separately, another sealed film was subjected to heat treatment at 50° C. for 7 days. The heat seal-starting temperature after heat treatment was measured using the heat treated specimen.

Izod impact strength (IZ)

The IZ is measured in accordance with ASTM D 256 at 23° C. using a notched specimen of 12.7 mm (width)×6.4 mm (thickness)×64 mm (length).

The specimen is prepared by injection molding at a resin temperature of 200° C. and a molding temperature of 40° C. using a polypropylene composition obtained by dry-blending 20% by weight of a polymer according to the present invention and 80% by weight of a polypropylene (HIPOL™, grade J 700, melt flow rate: 11 g/10 min (at 230° C.), density: 0.91, manufactured by Mitsui petrochemical Industries, Ltd.), and melt-kneading at 200° C. using a twin-screw extruder.

Film impact strength

The film impact strength is measured using a film impact tester (manufactured by Toyo Seiki K.K., diameter of impact head bulb: ½ inch (12.7 mm φ)).

Example 1

Synthesis of rac-dimethylsilyl-bis{1-(4-isopropyl-2, 7-dimethylindenyl)}zirconium dichloride Synthesis of 4-isopropyl-2,7-dimethylindene (compound 1)

A $^1$1-liter reactor thoroughly purged with nitrogen was charged with 90 g (0.67 mol) of aluminum chloride and 150 ml of carbon disulfide, and to the reactor was dropwise added a solution of 47 ml (0.30 mol) of p-cymene and 33 ml (0.3 mol) of methacryloyl chloride in 30 ml of carbon disulfide at a temperature of 20° to 25° C. The mixture was reacted at room temperature for 12 hours and then added to 1 kg of ice, followed by extraction with ether. The obtained ether solution was washed with saturated aqueous solution of sodium hydrogencarbonate and then water, and concentrated to obtain 68 g of an oil. This oil was purified by means of silica gel column chromatography (eluting solution: n-hexane) to obtain 42 g of a mixture (mixture 1) of 2,4-dimethyl-7-propyl-1-indanone and 2,7-dimethyl-4-isopropyl-1-indanone (yield: 67%).

A 1-liter reactor thoroughly purged with nitrogen was charged with 2.82 g (0.075 mol) of lithium aluminum hydride and 200 ml of ether, and to the reactor was dropwise added a mixture of 36.5 g (0.18 mol) of the mixture 1 and 150 ml of ether while cooling with ice. After the dropwise addition was completed, the mixture was stirred at room temperature for 30 minutes and then refluxed for 1 hour. After the reaction was completed, the reaction mixture was worked up by conventional procedure and then extracted with ether. The obtained ether solution was washed with saturated aqueous solution of sodium hydrogencarbonater and water, and dried over sodium sulfate. The ether layer was concentrated to obtain 36 g of a solid. This solid was slurried in 100 ml of n-hexane and the solvent was evaporated off to obtain 30 g of a mixture (mixture No. 2) of 2,4-dimethyl-7-isopropyl-1-indanol and 2,7-dimethyl-4-isopropyl-1-indanol (yield: 82%).

A 1-liter reactor thoroughly purged with nitrogen was charged with 25 g (0.12 mol) of the mixture 2 and 500 ml of benzene. To the reactor was added 50 mg (0.55 mmol) of paratoluene sulfonic acid monohydrate, and the mixture was refluxed for 1 hour. After the reaction was completed, the reaction mixture was poured into 30 ml of saturated sodium hydrogencarbonate solution. The resulting organic layer was washed with water and then dried over anhydrous sodium sulfate. The organic layer was concentrated to give an oil which was then distilled to obtain 20 g of the title compound 1 (yield: 90%).

The NMR data of the title compound 1 is shown in Table 1.

Synthesis of 1,1'-dimethylsilyl-bis(4-isopropyl-2,7-dimethylindene) (compound 2)

A 200-ml reactor thoroughly purged with nitrogen was charged with 9.5 g (51 mmol) of the title compound 1, 7.7 ml (51 mmol) of tetramethylethylenediamine and 60 ml of diethyl ether, followed by cooling to −10° C. To the solution was added a solution of n-butyllithium (51 mmol) in hexane. After heating to room temperature, the solution was cooled again to −10° C., 3.1 ml (25.5 mmol) of dimethyldichlorosilane was dropwise added over 30 minutes and the reaction was carried out for 1 hour. After the reaction was completed, the reaction solution was added to 40 ml of saturated aqueous solution of ammonium chloride, then extracted with n-hexane, washed with water and dried over magnesium sulfate. The salt was removed, and the resulting organic layer was concentrated under a reduced pressure to obtain an yellow oil which was purified by means of silica gel column chromatography (eluting solution: n-hexane) to obtain 5.4 g of the title compound 2 as a colorless amorphous product (yield: 50%).

The NMR data of the title compound 2 is shown in Table 1.

Synthesis of rac-dimethylsilyl-bis{1-(4-isopropyl-2, 7-dimethylindenyl)}zirconium dichloride (compound 3)

A 300-ml reactor thoroughly purged with nitrogen was charged with 5.4 g (12.6 mmol) of the title compound 2 and 100 ml of tetrahydrofuran, and the content in the reactor was cooled to −78° C. and stirred. To the reactor was dropwise added 16 ml of n-butyllithium (a solution in n-hexane, 1.58N, 25.2 mmol) over 20 minutes, and the mixture was stirred for another 1 hour with keeping the temperature to prepare an anion solution which was then slowly heated to room temperature.

Separately, 100 ml of tetrahydrofuran was charged in a 300-ml reactor thoroughly purged with nitrogen, cooled to −78° C. and stirred. To the reactor was slowly added 2.94 g (12.6 mmol) of zirconium tetrachloride, followed by heating to room temperature. To the mixture was dropwise added the anion solution prepared above over 30 minutes, followed by stirring at room temperature for 12 hours. After the reaction was completed, the reaction mixture was concentrated under a reduced pressure and a solid precipitated was washed three times with 300 ml of hexane to remove insoluble substances. The obtained hexane solution was concentrated to about 50 ml, and the solution was cooled at 6° C. for 12 hours. $^1$H-NMR analysis of the solid obtained, 1.78 g (yield: 24%), showed that it was a mixture of a racemic modification and a mesoisomer (4:1). This mixture was recrystallized from 100 ml of hexane to obtain 0.22 g of the title compound 3 as an yellow prismatic crystal (yield: 3%). The result of the FD mass spectrometry of the title compound 3 was 588 ($M^+$).

The NMR data of the title compound 3 is shown in Table 1.

Example 2

Synthesis of rac-diphenylsilyl-bis{1-(4-isopropyl-2, 7-dimethylindenyl)}zirconium dichloride Synthesis of 1,1'-diphenylsilyl-bis(4-isopropyl-2,7-dimethylindene) (compound 4)

The procedure of the synthesis of the title compound 2 in Example 1 was repeated except that 120 mg of copper cyanide was used in place of tetramethylethylenediamine and 5.7 ml of diphenyldichlorosilane in place of dimethyldichlorosilane.

The title compound 4 was obtained as a colorless amorphous product in an amount of 7.2 g (yield: 49%).

The NMR data of the title compound 4 is shown in Table 1.

Synthesis of rac-diphenylsilyl-bis{1-(4-isopropyl-2, 7-dimethylindenyl)}zirconium dichloride (compound 5)

The procedure of the synthesis of the title compound 3 in Example 1 was repeated except that 7.1 g (12.9 mmol) of the title compound 4 was used in place of the title compound 2 and 3.01 of zirconium tetrachloride in place of 2.94 g.

The title compound 5 was obtained as an yellow prismatic crystal in an amount of 1.10 g (yield: 12%). The result of the FD mass spectrometry of the compound 5 was 712 ($M^+$).

The NMR data of the title compound 5 is shown in Table 1.

TABLE 1

NMR Data

| Compound No. | $^1$H-NMR Spectrum (CDCl$_3$, ppm) |
|---|---|
| 1 | 1.26(6H, d, J=7.2Hz), 2.70(3H, s), 2.38(3H, s), 2.88(1H, q, J=7.0Hz), 3.27(2H, s), 6.54(1H, s), 6.90(1H, s), 7.10(1H, s) |
| 2 | 1.60(12H, d, J=7.2Hz), 0.94~1.14(6H, m), 1.91~2.06(6H, m), 2.26(6H, s), 2.71(2H, q, J=7.2Hz), 3.49(2H, s), 6.49(2H, s), 6.74(2H, s), 7.06(2H, s) |
| 3 | 1.20(12H, d, J=7.2Hz), 1.29(6H, s), 2.21(6H, s), 2.33(6H, s), 2.81(2H, q, J=7.0Hz), 6.70(2H, s), 7.01(2H, s), 7.26(2H, s) |
| 4 | 1, 06(6H, d, J=7.2Hz), 1.26(6H, d, J=7.2Hz), 1.80(3H, s), 2.10(6H, s), 2.24(3H, s), 2.80(2H, s), 4.36(4H, br.s), 6.16(2H, s), 6.60–7.68(14H, m) |
| 5 | 0.92(12H, d, J=6.8Hz), 2.02(6H, s), 2.36(6H, s), 2.60(2H, q, J=6.8Hz), 6.80(2H, s), 6.90(2H, s), 6.99(2H, s), 7.45–7.50(6H, m), 8.12–8.16(4H, m) |

Example 3

A 2-liter autoclave thoroughly purged with nitrogen was charged with 500 g of propylene, followed by warming to 40° C. To the autoclave were added 0.2 mmol of triisobutylaluminum, 0.2 mmol of methylaluminoxane and 0.001 mmol (in terms of Zr atom) of rac-dimethylsilyl-bis{1-(2,7-dimethyl-4-isopropyl-1-indenyl)}zirconium dichloride to polymerize propylene at 50° C. for 1 hour. After the polymerization, the autoclave was released to remove propylene, and the resulting polymer was dried at 80° C. for 10 hours.

The amount of the polymer obtained was 158 g and the polymerization activity was 158 kg-PP/mmol-Zr. The polymer had an [η] of 4.55 dl/g, a Mw/Mn of 2.2, an mmmm pentad value of 95.5%, a proportion of the 2,1-insertion of 0.90% and a Tm of 147° C.

Example 4

A 2-liter autoclave thoroughly purged with nitrogen was charged with 500 g of propylene, followed by warming to 40° C. To the autoclave were added 0.2 mmol of triethylaluminum, 0.001 mmol (in terms of Zr atom) of rac-diphenylsilyl-bis{-(2,7-dimethyl-4-isopropylindenyl)}zirconium dichloride and 0.002 mmol (in terms of B atom) of tris(pentafluorophenyl)boron to polymerize propylene at 50° C. for 1 hour. After the polymerization, the autoclave was released to remove propylene, and the resulting polymer was dried at 80° C. for 10 hours.

The amount of the polymer obtained was 94 g and the polymerization activity was 94 kg-PP/mmol-Zr. The polymer had an [η] of 4.75 dl/g, a Mw/Mn of 2.3, an mmmm pentad value of 96.4%, a proportion of the 2,1-insertion of 0.80% and a Tm of 148° C.

Comparative Example 1

A 2-liter autoclave thoroughly purged with nitrogen was charged with 500 g of propylene, followed by warming to 40° C. To the autoclave were added 0.2 mmol of triisobutylaluminum, 0.2 mmol of methylaluminoxane and 0.001 mmol (in terms of Zr atom) of rac-dimethylsilyl-bis{1-(2-methyl-4-isopropylindenyl)}zirconium dichloride to polymerize propylene at 50° C. for 1 hour. After the polymerization, the autoclave was released to remove propylene, and the resulting polymer was dried at 80° C. for 10 hours.

The amount of the polymer obtained was 125 g and the polymerization activity was 125 kg-PP/mmol-Zr. The polymer had an [η] of 3.47 dl/g, a Mw/Mn of 2.1, an mmmm pentad value of 96.2%, a proportion of the 2,1-insertion of 0.40 and a Tm of 152° C.

Example 5

A 1-liter glass reactor thoroughly purged with nitrogen was charged with 500 ml of toluene, and propylene was fed at a rate of 100 liters/hr, followed by warming to 50° C. To the reactor was added a solution obtained by precontacting 3.5 mmol of methylaluminoxane and 0.01 mmol (in terms of Zr atom) of rac-dimethylsilyl-bis{1-(2,7-dimethyl-4-isopropylindenyl)}zirconium dichloride in toluene, to polymerize propylene at 50° C. for 20 minutes. After the polymerization, the solution was poured in a methanol-hydrochloric acid solution, and the resulting mixture was filtered to give a polymer which was dried at 80° C. for 10 hours.

The amount of the polymer obtained was 32.6 g and the polymerization activity was 8.2 kg-PP/mmol-Zr. The polymer had an [η] of 1.37 dl/g, a Mw/Mn of 2.2 and a Tm of 148° C.

Comparative Example 2

The procedures of Example 5 were repeated except that rac-ethylenebis{1-(2,4,7-trimethylindenyl)}zirconium dichloride was used in place of rac-dimethylsilyl-bis{(1-(2,7-dimethyl-4-isopropylindenyl)}zirconium dichloride.

The amount of the polymer obtained was 23.1 g and the polymerization activity was 5.8 kg-PP/mmol-Zr. The polymer had an [η] of 0.44 dl/g, a Mw/Mn of 2.3 and a Tm of 150° C. This polymer had a molecular weight extremely lower than that of the polymer obtained in Example 5.

Example 6

Preparation of solid catalyst Component (a)

A 500-ml reactor thoroughly purged with nitrogen was charged with 25 g of silica (F-948, available from Fuji Devison Co.) having been dried at 200° C. for 6 hours in a stream of nitrogen and 310 ml of toluene, and the system was set to 0° C. with stirring. To the system was dropwise added 90 ml of an organoaluminum oxy-compound (methylaluminoxane available from Schering Co., diluted in toluene, 2.1 mol/liter) over 60 minutes in a nitrogen atmosphere. Then, the mixture was reacted at the same temperature for 30 minutes and further at 90° C. for 4 hours. The reaction system was allowed to cool and when the temperature was reached to 60° C., the supernatant was decantated off and the residue was washed three times with 150 ml of toluene at room temperature to obtain a solid catalyst component (a) containing 6.8 mmol of Al per 1 g of silica.

Preparation of solid catalyst component (b)

A 200-ml reactor thoroughly purged with nitrogen was charged with 50 ml of n-hexane, and to the reactor were added 10.5 mmol (in terms of Al atom) of the solid catalyst component (a) obtained above and 0.03 mmol (in terms of Zr atom) of rac-dimethylsilyl-bis{1-(2,7-dimethyl-4-isopropylindenyl)}zirconium dichloride, followed by stirring for 20 minutes. Then, 100 ml of n-hexane and 0.9 mmol of triisobutylaluminum were successively added to the reactor and the mixture was stirred for 10 minutes. Thereafter, a propylene gas (2.2 liters/hr) was passed through the reactor at 20° C. for 4 hours to prepolymerize propylene. The supernatant was decantated off and then the residue washed three times with 150 ml of toluene to obtain a solid catalyst component (b) in which Zr and Al were supported in amounts of 0.011 mmol and 4.48 mmol, respectively, per 1 g of the solid catalyst.

Polymerization 750 ml of purified n-hexane was introduced into a 2-liter autoclave thoroughly purged with nitrogen, and stirred at 25° C. for 20 minutes in a propylene/ethylene mixed gas atmosphere (ethylene: 3.6% by mol). To the reaction system were added 1.0 mmol of triisobutylaluminum and 0.002 mmol (in terms of Zr atom) of the solid catalyst component (b), and the temperature of the system was elevated to 50° C. to polymerize the monomers for 1 hour at a total pressure of 2 kg/cm$^2$-G. After the polymerization, the reaction mixture was filtered to remove the solvent, the resulting polymer was washed with hexane and dried at 80° C. for 10 hours.

The amount of the polymer (powder) obtained was 75 g, the amount (SP) of the polymer dissolved in the solvent was 1.9 g (2.5% by weight), and the polymerization activity was 38.5 kg-copolymer/mmol-Zr. The polymer powder had an MFR of 6.0 dg/min, a Mw/Mn of 2.6, an ethylene content of 2.9% by mol and a Tm of 126° C.

Example 7

Preparation of solid catalyst component (c)

A 200-ml reactor thoroughly purged with nitrogen was charged with 50 ml of n-hexane, and to the reactor were added 10.5 mmol (in terms of Al atom) of the solid catalyst component (a) obtained above and 0.03 mmol (in terms of Zr atom) of rac-diphenylsilyl-bis{1-(2,7-dimethyl-4-isopropylindenyl)}zirconium dichloride, followed by stirring for 20 minutes. Then, 100 ml of n-hexane and 0.9 mmol of triisobutylaluminum were successively added to the reactor, and the mixture was stirred for 10 minutes. Thereafter, propylene gas (2.2 liters/hr) was passed through the reactor at 20° C. for 4 hours to polymerize propylene. The supernatant was decantated off, and then the residue was washed three times with 150 ml of toluene to obtain a solid catalyst component (c) in which Zr and Al were supported in amounts of 0.011 mmol and 4.55 mmol, respectively, per 1 g of the solid catalyst.

Polymerization 750 ml of purified n-hexane was introduced into a 2-liter autoclave thoroughly purged with nitrogen, and stirred at 25° C. for 20 minutes in a propylene/ethylene mixed gas atmosphere (ethylene: 3.6% by mol). To the reaction system were added 1.0 mmol of triisobutylaluminum and 0.002 mmol (in terms of Zr atom) of the solid catalyst component (c), and the temperature of the system was elevated to 50° C. to polymerize the monomers for 1 hour at a total pressure of 2 kg/cm$^2$-G. After the polymerization, the reaction mixture was filtered to remove the solvent, the resulting polymer was washed with hexane and dried at 80° C. for 10 hours.

The amount of the polymer (powder) obtained was 59 g, the amount (SP) of the polymer dissolved in the solvent was 2.5 g (4.0% by weight), and the polymerization activity was 30.7 kg-copolymer/mmol-Zr. The polymer powder had an MFR of 5.8 dg/min, a Mw/Mn of 2.6, an ethylene content of 2.9% by mol and a Tm of 127° C.

Comparative Example 3

Preparation of solid catalyst component (d)

A 200-ml reactor thoroughly purged with nitrogen was charged with 50 ml of n-hexane, and to the reactor were added 10.5 mmol (in terms of Al atom) of the solid catalyst component (a) obtained above and 0.03 mmol (in terms of Zr atom) of rac-dimethylsilyl-bis{1-(2-methyl-4-isopropylindenyl)}zirconium dichloride, followed by stirring for 20 minutes. Then, 100 ml of n-hexane and 0.09 mmol of triisobutylaluminum were successively added to the reactor, and the mixture was stirred for 10 minutes. Thereafter, a propylene gas (2.2 liters/hr) was passed through the reactor at 20° C. for 4 hours to prepolymerize propylene. The supernatant was decantated off, and then the residue was washed three times with 150 ml of toluene to obtain a solid catalyst component (d) in which Zr and Al were supported in amounts of 0.011 mmol and 4.35 mmol, respectively, per 1 g of the solid catalyst.

Polymerization 750 ml of purified n-hexane was introduced into a 2-liter autoclave thoroughly purged with nitrogen, and stirred at 25° C. for 20 minutes in a propylene/ethylene mixed gas atmosphere (ethylene: 5.2% by mol). To the reaction system were added 1.0 mmol of triisobutylaluminum and 0.002 mmol (in terms of Zr atom) of the solid catalyst component (d), and the temperature of the system was elevated to 50° C. to polymerize the monomers for 1 hour at a total pressure of 2 kg/cm$^2$-G. After the polymerization, the reaction mixture was filtered to remove the solvent, the resulting polymer was washed with hexane and dried at 80° C. for 10 hours.

The amount of polymer (powder) obtained was 67 g, and a small amount of the polymer adhered to the autoclave wall was observed. The amount (SP) of the polymer dissolved in the solvent was 9.0 g (12.0% by weight). The polymerization activity was 38 kg-copolymer/mmol-Zr. The polymer powder had an MFR of 12 dg/min, a Mw/Mn of 2.5, an ethylene content of 5.0% by mol and a Tm of 127° C.

When the above polymerization procedure is performed in an industrial scale, it it presumed that the polymer adhered to the autoclave wall causes a reduced heat transfer efficiency, and the high SP value causes not only a reduced polymer yield but also an increased viscosity of the solvent removed, resulting in difficult operation.

Example 8

A 2-liter autoclave thoroughly purged with nitrogen was charged with 500 g of propylene. The temperature of the autoclave was elevated to 40° C., and to the autoclave were added 0.2 mmol of triisobutylaluminum, 0.2 mmol of methylamuminoxane and 0.001 mmol (in terms of Zr atom) of rac-diphenylsilyl-bis{1-(2,7-dimethyl-4-isopropylindenyl)}zirconium dichloride, to polymerize propylene at 50° C. for 1 hour. After the polymerization, the autoclave was released to remove propylene, and the resulting polymer was dried at 80° C. for 10 hours under a reduced pressure.

The amount of the propylene polymer obtained was 158 g, and the polymerization activity was 158 kg-polymer/mmol-Zr. The polymer had an intrinsic viscosity [η] of 4.55 dl/g. In the propylene polymer, the triad tacticity of the propylene unit chain consisting of head-to-tail bonds was 95.4%, the proportion of the inversely inserted units based on the 2,1-insertion of the propylene monomer was 0.87%, and the proportion of the inversely inserted units based on the 1,3-insertion of the propylene monomer was not more than 0.03%.

The polymer had a melt flow rate (MFR) of 12.5 g/10 min, a flexural modulus (FM) of 12500 kg/cm$^2$, and a heat distortion temperature of 105° C.

Example 9

750 ml of hexane was introduced into a 2-liter autoclave thoroughly purged with nitrogen and stirred at 25° C. for 20 minutes in a propylene/ethylene mixed gas atmosphere (ethylene: 2.9% by mol). To the reaction system were added 0.25 mmol of triisobutylaluminum, 0.5 mmol of methylaluminoxane and 0.0015 mmol (in terms of Zr atom) of rac-diphenylsilyl-bis{1-(2,7-dimethyl-4-isopropylindenyl)}zirconium dichloride, and the temperature of the system was elevated to 50° C. to polymerize the monomers for 1 hour while keeping the total pressure at 2 kg/cm$^2$-G. After the polymerization, the autoclave was released, the resulting polymer was recovered in a large amount of methanol and dried at 80° C. for 10 hours under a reduced pressure.

The amount of the propylene copolymer obtained was 26.9 g, and the polymerization activity was 17.9 kg-polymer/mmol-Zr. The copolymer had an intrinsic viscosity [η] of 2.2 dl/g and an ethylene content of 3.0% by mol. In the propylene copolymer, the triad tacticity of of the propylene unit chain consisting of head-to-tail bonds was 97.3%, the proportion of the inversely inserted units based on the 2,1-insertion of the propylene monomer was 0.9%, and the proportion of the inversely inserted units based on the 1,3-insertion of the propylene monomer was 0.04%.

The film of the copolymer had heat sel-starting temperature of 118° C. and a heat seal-starting temperature after heat treatment of 120° C.

The results are shown in Table 2.

Example 10

900 ml of hexane was introduced into a 2-liter autoclave thoroughly purged with nitrogen, and 1 mmol of triisobutylaluminum was added thereto. After elevating the temperature of the reaction system to 70° C., ethylene was fed to the system to a pressure of 1.5 kg/cm$^2$, and propylene was then fed to a total pressure of 8 kg/cm$^2$-G. Then, to the reaction system were added 0.3 mmol of methylaluminoxane and 0.001 mmol (in terms of Zr atom) of rac-dimethylsilyl-bis{1-(2,7-dimethyl-4-isopropylindenyl)}zirconium dichloride to polymerize monomers for 20 minutes while propylene was continuously fed to keep the total pressure at 8 kg/cm$^2$-G. After the polymerization, the autoclave was released, the resulting polymer was recovered in a large amount of methanol and dried at 110° C. for 10 hours under a reduced pressure.

The amount of the propylene copolymer obtained was 21.2 g, and the polymerization activity was 21 kg-polymer/mmol-Zr. The copolymer had an intrinsic viscosity [η] of 1.5 dl/g and an ethylene content of 4.7% by mol. In the propylene copolymer, the triad tacticity of the propylene unit chain consisting of head-to-tail bonds was 96.9%, the proportion of the inversely inserted units based on the 2,1-insertion of the propylene monomer was 1.1%, and the proportion of the inversely inserted units based on the 1,3-insertion of the propylene monomer was not more than 0.04%.

The film of the copolymer had a heat seal-starting temperature of 107° C. and a heat seal-starting temperature after heat treatment of 111° C.

The results are shown in Table 2.

Example 11

900 ml of hexane was introduced into a 2-liter autoclave thoroughly purged with nitrogen. Then, to the autoclave was added 1 mmol of triisobutylaluminum and was fed 60 liters of propylene gas. After elevating the temperature of the reaction system to 70° C., ethylene was fed to the system to a total pressure of 8 kg/cm$^2$-G. Then, to the reaction system were added 0.45 mmol of methylaluminoxane and 0.0015 mmol (in terms of Zr atom) of rac-diphenylsilyl-bis{1-(2,7-dimethyl-4-isopropylindenyl)}zirconium dichloride to polymerize the monomers for 40 minutes while ethylene was continuously fed to keep the total pressure at 8 kg/cm$^2$-G. After the polymerization, the autoclave was released, the resulting polymer was recovered in a large amount of methanol, and dried at 110° C. for 10 hours under a reduced pressure.

The amount of the polymer obtained was 47.2 g. The polymerization activity was 31.5 kg-polymer/mmol-Zr. The polymer had an intrinsic viscosity [η] of 2.0 dl/g and an ethylene content of 27.0% by mol. In the polymer, the triad tacticity of the propylene unit chain consisting of head-to-tail bonds was 95.4%, the proportion of the inversely inserted units based on the 2,1-insertion of the propylene monomer was 0.88%, and the proportion of the inversely inserted units based on the 1,3-insertion of the propylene monomer was not more than 0.05%.

The film of the copolymer had a film impact strength of 6000 kgf.cm/cm, and the composition with polypropylene had IZ of 35 kg.cm/cm and a melt flow rate (MFR) of 9.3 g/10 min.

The results are shown in Table 2.

Example 12

900 ml of hexane was introduced into a 2-liter autoclave thoroughly purged with nitrogen, and 1 mmol of triisobutylaluminum was added thereto. After elevating the temperature of the reaction system to 70° C., ethylene was fed to the system to a pressure of 2.0 kg/cm$^2$, and then propylene was fed to the system to a total pressure of 8 kg/cm$^2$-G. Then, to the reaction system were added 0.3 mmol of methylaluminoxane and 0.001 mmol (in terms of Zr atom) of rac-dimethylsilyl-bis{1-(2,7-dimethyl-4-isopropylindenyl)}zirconium dichloride, to polymerize the monomers for 10 minutes while propylene was continuously fed to keep the total pressure at 8 kg/cm$^2$-G. After the polymerization, the autoclave was released, the resulting polymer was recovered in a large amount of methanol and dried at 110° C. for 10 hours under a reduced pressure.

The amount of the polymer obtained was 16.8 g and the polymerization activity was 16.8 kg-polymer/mmol-Zr. The polymer had an intrinsic viscosity [η] of 1.7 dl/g and an ethylene content of 8.5% by mol. In the polymer, the triad tacticity of the propylene unit chain consisting of head-to-tail bonds was 95.6%, the proportion of the inversely inserted units based on the 2,1-insertion of the propylene monomer was 0.62%, and the proportion of the inversely inserted units based on the 1,3-insertion of the propylene monomer was not more than 0.05%.

The film of the copolymer had a heat seal-starting temperature of 90° C. and a heat seal-starting temperature after heat treatment of 93° C.

The results are shown in Table 2.

TABLE 2

| Example | Intrinsic viscosity [η] | Melting point (°C.) | Ethylene content (mol %) | Heat seal-starting temperature (°C.) | Heat seal-starting temperature after heat treatment | Film impact strength (kg · cm/ cm) |
|---|---|---|---|---|---|---|
| Ex. 9 | 2.2 | 120 | 3 | 118 | 120 | — |
| Ex. 10 | 1.5 | 110 | 4.7 | 107 | 111 | — |
| Ex. 11 | 2 | — | 27 | — | — | 6000 |
| Ex. 12 | 1.7 | 90 | 8.5 | 90 | 93 | — |

| Example | IZ of composition with polypropylene (kgf · cm/cm) | MFR of composition with polypropylene (g/10 min) |
|---|---|---|
| Ex. 9 | — | — |
| Ex. 10 | — | — |
| Ex. 11 | 35 | 9.3 |
| Ex. 12 | — | — |

What is claimed is:

1. A transition metal compound represented by the following formula:

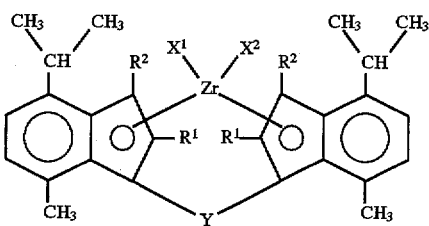

wherein $R^1$ and $R^2$ are each a hydrogen atom or a hydrocarbon group of 1 to 3 carbon atoms;

$X^1$ and $X^2$ are each a halogen atom; and

Y is a divalent silicon-containing group selected from the group consisting of dimethylsilylene, diphenylsilylene and methylphenylsilylene.

2. The transition metal compound according to claim 1, wherein:

$R^1$ is methyl; and $R^2$ is hydrogen.

3. The compound dimethylsilyl-bis(1-(4-isopropyl-2,7-dimethylindenyl)zirconium dichloride.

4. The compound diphenylsilyl-bis(1-(4-isopropyl-2,7-dimethylindenyl)zirconium dichloride.

* * * * *